US008992604B2

(12) United States Patent
Gross et al.

(10) Patent No.: US 8,992,604 B2
(45) Date of Patent: Mar. 31, 2015

(54) TECHNIQUES FOR PERCUTANEOUS MITRAL VALVE REPLACEMENT AND SEALING

(75) Inventors: Yossi Gross, Moshav Mazor (IL); Gil Hacohen, Raanana (IL); Eran Miller, Moshav Beit Elazari (IL); Yuval Zipory, Modi'in (IL); Tal Reich, Binyamina (IL)

(73) Assignee: Mitraltech Ltd., Or Yehuda (IL)

( * ) Notice: Subject to any disclaimer, the term of this patent is extended or adjusted under 35 U.S.C. 154(b) by 0 days.

(21) Appl. No.: 13/033,852

(22) Filed: Feb. 24, 2011

(65) Prior Publication Data
US 2012/0022640 A1 Jan. 26, 2012

Related U.S. Application Data

(63) Continuation-in-part of application No. 12/840,463, filed on Jul. 21, 2010.

(51) Int. Cl.
*A61F 2/24* (2006.01)
*A61B 17/068* (2006.01)
(Continued)

(52) U.S. Cl.
CPC ............... *A61F 2/2418* (2013.01); *A61F 2/243* (2013.01); *A61F 2/24* (2013.01); *A61F 2/2427* (2013.01); *A61B 17/068* (2013.01); *A61B 17/29* (2013.01); *A61B 2017/00243* (2013.01); *A61B 2017/0441* (2013.01); *A61B 2017/0647* (2013.01); *A61B 2017/0649* (2013.01); *A61F 2/2409* (2013.01); *A61F 2/2436* (2013.01); *A61F 2/2439* (2013.01); *A61F 2250/006* (2013.01); *A61F 2250/0063* (2013.01); *A61B 2017/0464* (2013.01); *A61F 2/2412* (2013.01);
(Continued)

(58) Field of Classification Search
USPC ............. 623/2.1, 2.11, 2.12, 2.17, 2.18, 2.36, 623/2.37, 2.38, 2.4, 2.41, 2.42, 904
See application file for complete search history.

(56) References Cited

U.S. PATENT DOCUMENTS 4,261,342 A 4/1981 Aranguren Duo
5,108,420 A 4/1992 Marks
(Continued)

FOREIGN PATENT DOCUMENTS

EP 1 264 582 A2 12/2002
WO 99/30647 A1 6/1999
(Continued)

OTHER PUBLICATIONS

An International Search Report and a Written Opinion both dated Oct. 113, 2011 which issued during the prosecution of Applicant's PCT/IL11/00231.
(Continued)

*Primary Examiner* — Dianne Dornbuscch
*Assistant Examiner* — Robert Lynch
(74) *Attorney, Agent, or Firm* — Ladas & Parry LLP

(57) ABSTRACT

Apparatus and methods are described, including one or more valve support guide members that are delivered to one or more commissures of a native atrioventricular valve of a patient. A prosthetic valve support is advanced toward the native valve along the one or more valve support guide members and placed at the native valve. A prosthetic valve is coupled to the valve support. One or more sealing elements facilitate sealing of an interface between the prosthetic valve support and the native valve. Other applications are also described.

12 Claims, 28 Drawing Sheets

(51) Int. Cl.
  *A61B 17/29* (2006.01)
  *A61B 17/00* (2006.01)
  *A61B 17/04* (2006.01)
  *A61B 17/064* (2006.01)

(52) U.S. Cl.
  CPC ...... *A61F 2/2457* (2013.01); *A61F 2220/0016* (2013.01); *A61F 2230/005* (2013.01); *A61F 2230/0054* (2013.01)
  USPC ........................................ 623/2.11; 623/2.17

(56) References Cited

U.S. PATENT DOCUMENTS

| | | | |
|---|---|---|---|
| 5,607,444 A | 3/1997 | Lam | |
| 5,607,470 A | 3/1997 | Milo | |
| 5,868,777 A | 2/1999 | Lam | |
| 6,074,417 A | 6/2000 | Peredo | |
| 6,113,612 A | 9/2000 | Swanson et al. | |
| 6,120,534 A | 9/2000 | Ruiz | |
| 6,152,937 A | 11/2000 | Peterson et al. | |
| 6,287,339 B1 | 9/2001 | Vazquez et al. | |
| 6,332,893 B1 | 12/2001 | Mortier et al. | |
| 6,391,036 B1 | 5/2002 | Berg et al. | |
| 6,402,780 B2 | 6/2002 | Williamson, IV et al. | |
| 6,409,755 B1 | 6/2002 | Vrba | |
| 6,419,696 B1 | 7/2002 | Ortiz et al. | |
| 6,428,550 B1 | 8/2002 | Vargas et al. | |
| 6,440,164 B1 | 8/2002 | DiMatteo et al. | |
| 6,458,153 B1 | 10/2002 | Bailey et al. | |
| 6,511,491 B2 | 1/2003 | Grudem et al. | |
| 6,530,952 B2 | 3/2003 | Vesely | |
| 6,540,782 B1 | 4/2003 | Snyders | |
| 6,558,418 B2 | 5/2003 | Carpentier et al. | |
| 6,602,263 B1 | 8/2003 | Swanson et al. | |
| 6,616,675 B1 | 9/2003 | Evard et al. | |
| 6,699,256 B1 | 3/2004 | Logan et al. | |
| 6,716,244 B2 | 4/2004 | Klaco | |
| 6,719,781 B1 | 4/2004 | Kim | |
| 6,730,118 B2 | 5/2004 | Spenser et al. | |
| 6,767,362 B2 | 7/2004 | Schreck | |
| 6,830,585 B1 | 12/2004 | Artof et al. | |
| 6,830,638 B2 | 12/2004 | Boylan et al. | |
| 6,960,217 B2 | 11/2005 | Bolduc | |
| 6,964,684 B2 | 11/2005 | Ortiz et al. | |
| 7,018,406 B2 | 3/2006 | Seguin et al. | |
| 7,041,132 B2 | 5/2006 | Quijano et al. | |
| 7,077,861 B2 | 7/2006 | Spence | |
| 7,101,395 B2 | 9/2006 | Tremulis et al. | |
| 7,198,646 B2 | 4/2007 | Figulla et al. | |
| 7,201,772 B2 | 4/2007 | Schwammenthal et al. | |
| 7,288,111 B1 | 10/2007 | Holloway et al. | |
| 7,335,213 B1 | 2/2008 | Hyde et al. | |
| 7,404,824 B1 | 7/2008 | Webler et al. | |
| 7,422,603 B2 | 9/2008 | Lane | |
| 7,429,269 B2 | 9/2008 | Schwammenthal et al. | |
| 7,442,204 B2 | 10/2008 | Schwammenthal et al. | |
| 7,445,630 B2 | 11/2008 | Lashinski et al. | |
| 7,455,677 B2 | 11/2008 | Vargas et al. | |
| 7,455,688 B2 | 11/2008 | Furst et al. | |
| 7,462,162 B2 | 12/2008 | Phan et al. | |
| 7,481,838 B2 | 1/2009 | Carpentier et al. | |
| 7,510,575 B2 | 3/2009 | Spenser et al. | |
| 7,527,646 B2 | 5/2009 | Rahdert et al. | |
| 7,582,111 B2 | 9/2009 | Krolik et al. | |
| 7,585,321 B2 | 9/2009 | Cribier | |
| 7,632,302 B2 | 12/2009 | Vreeman et al. | |
| 7,717,955 B2 | 5/2010 | Lane et al. | |
| 7,731,741 B2 | 6/2010 | Eidenschink | |
| 7,771,467 B2 | 8/2010 | Svensson | |
| 7,771,469 B2 | 8/2010 | Liddicoat | |
| 7,780,726 B2 | 8/2010 | Seguin | |
| 7,799,069 B2 | 9/2010 | Bailey et al. | |
| 7,803,181 B2 | 9/2010 | Furst et al. | |
| 7,837,727 B2 | 11/2010 | Goetz et al. | |
| 7,842,081 B2 | 11/2010 | Yadin | |
| 7,850,725 B2 | 12/2010 | Vardi et al. | |
| 7,871,432 B2 | 1/2011 | Bergin | |
| 7,871,436 B2 | 1/2011 | Ryan et al. | |
| 7,887,583 B2 | 2/2011 | Macoviak | |
| 7,892,281 B2 | 2/2011 | Seguin et al. | |
| 7,896,915 B2 | 3/2011 | Guyenot et al. | |
| 7,914,544 B2 | 3/2011 | Nguyen et al. | |
| 7,914,569 B2 | 3/2011 | Nguyen et al. | |
| 7,927,370 B2 | 4/2011 | Webler et al. | |
| 7,947,072 B2 | 5/2011 | Yang et al. | |
| 7,947,075 B2 | 5/2011 | Goetz et al. | |
| 7,955,375 B2 | 6/2011 | Agnew | |
| 7,955,384 B2 | 6/2011 | Rafiee et al. | |
| 7,967,833 B2 | 6/2011 | Sterman et al. | |
| 7,967,857 B2 | 6/2011 | Lane | |
| 7,981,151 B2 | 7/2011 | Rowe | |
| 7,981,153 B2 | 7/2011 | Fogarty et al. | |
| 7,992,567 B2 | 8/2011 | Hirotsuka et al. | |
| 7,993,393 B2 | 8/2011 | Carpentier et al. | |
| 8,002,825 B2 | 8/2011 | Letac et al. | |
| 8,016,877 B2 | 9/2011 | Seguin et al. | |
| 8,016,882 B2 | 9/2011 | Macoviak et al. | |
| 8,021,420 B2 | 9/2011 | Dolan | |
| 8,021,421 B2 | 9/2011 | Fogarty et al. | |
| 8,029,564 B2 | 10/2011 | Johnson et al. | |
| 8,034,104 B2 | 10/2011 | Carpentier et al. | |
| 8,043,360 B2 | 10/2011 | McNamara et al. | |
| 8,048,140 B2 | 11/2011 | Purdy | |
| 8,048,153 B2 | 11/2011 | Salahieh et al. | |
| 8,052,741 B2 | 11/2011 | Bruszewski et al. | |
| 8,057,532 B2 | 11/2011 | Hoffman | |
| 8,057,540 B2 | 11/2011 | Letac et al. | |
| 8,062,355 B2 | 11/2011 | Figulla et al. | |
| 8,062,359 B2 | 11/2011 | Marquez et al. | |
| 8,070,708 B2 | 12/2011 | Rottenberg et al. | |
| 8,070,800 B2 | 12/2011 | Lock et al. | |
| 8,070,802 B2 | 12/2011 | Lamphere et al. | |
| 8,070,804 B2 | 12/2011 | Hyde et al. | |
| 8,075,611 B2 | 12/2011 | Millwee et al. | |
| 8,080,054 B2 | 12/2011 | Rowe | |
| 8,092,518 B2 | 1/2012 | Schreck | |
| 8,092,520 B2 | 1/2012 | Quadri | |
| 8,092,521 B2 | 1/2012 | Figulla et al. | |
| 8,105,377 B2 | 1/2012 | Liddicoat | |
| 8,118,866 B2 | 2/2012 | Herrmann et al. | |
| 8,136,218 B2 | 3/2012 | Millwee et al. | |
| 8,137,398 B2 | 3/2012 | Tuval et al. | |
| 8,142,492 B2 | 3/2012 | Forster et al. | |
| 8,142,494 B2 | 3/2012 | Rahdert et al. | |
| 8,142,496 B2 | 3/2012 | Berreklouw | |
| 8,142,497 B2 | 3/2012 | Friedman | |
| 8,147,504 B2 | 4/2012 | Ino et al. | |
| 8,157,852 B2 | 4/2012 | Bloom et al. | |
| 8,157,853 B2 | 4/2012 | Laske et al. | |
| 8,157,860 B2 | 4/2012 | McNamara et al. | |
| 8,163,014 B2 | 4/2012 | Lane et al. | |
| 8,167,894 B2 | 5/2012 | Miles et al. | |
| 8,167,932 B2 | 5/2012 | Bourang et al. | |
| 8,167,935 B2 | 5/2012 | McGuckin, Jr. et al. | |
| 8,172,896 B2 | 5/2012 | McNamara et al. | |
| 8,177,836 B2 | 5/2012 | Lee et al. | |
| 8,182,528 B2 | 5/2012 | Salahieh et al. | |
| 8,211,169 B2 | 7/2012 | Lane et al. | |
| 8,221,492 B2 | 7/2012 | Case et al. | |
| 8,221,493 B2 | 7/2012 | Boyle et al. | |
| 8,226,710 B2 | 7/2012 | Nguyen et al. | |
| 8,231,670 B2 | 7/2012 | Salahieh et al. | |
| 8,236,045 B2 | 8/2012 | Benichou et al. | |
| 8,236,049 B2 | 8/2012 | Rowe et al. | |
| 8,252,042 B2 | 8/2012 | McNamara et al. | |
| 8,252,051 B2 | 8/2012 | Chau et al. | |
| 8,252,052 B2 | 8/2012 | Salahieh et al. | |
| 8,257,390 B2 | 9/2012 | Carley et al. | |
| 8,277,501 B2 | 10/2012 | Chalekian et al. | |
| 8,287,591 B2 | 10/2012 | Keidar et al. | |
| 8,298,280 B2 | 10/2012 | Yadin et al. | |
| 8,308,798 B2 | 11/2012 | Pintor et al. | |
| 8,317,853 B2 | 11/2012 | Agnew | |
| 8,317,855 B2 | 11/2012 | Gregorich et al. | |

(56) References Cited

U.S. PATENT DOCUMENTS

| | | |
|---|---|---|
| 8,323,335 B2 | 12/2012 | Rowe et al. |
| 8,328,868 B2 | 12/2012 | Paul et al. |
| 8,343,174 B2 | 1/2013 | Goldfarb et al. |
| 8,430,934 B2 | 4/2013 | Das |
| 8,449,625 B2 | 5/2013 | Campbell et al. |
| 8,628,571 B1 | 1/2014 | Hacohen et al. |
| 8,696,742 B2 | 4/2014 | Pintor et al. |
| 2001/0021872 A1 | 9/2001 | Bailey et al. |
| 2002/0151970 A1 | 10/2002 | Garrison et al. |
| 2003/0036791 A1 | 2/2003 | Philipp et al. |
| 2003/0074052 A1 | 4/2003 | Besselink |
| 2003/0083742 A1 | 5/2003 | Spence et al. |
| 2003/0105519 A1 | 6/2003 | Fasol et al. |
| 2003/0158578 A1 | 8/2003 | Pantages et al. |
| 2004/0039414 A1 | 2/2004 | Carley et al. |
| 2004/0093060 A1 | 5/2004 | Seguin et al. |
| 2004/0122514 A1 | 6/2004 | Fogarty et al. |
| 2004/0176839 A1 | 9/2004 | Huynh et al. |
| 2004/0186565 A1 | 9/2004 | Schreck |
| 2004/0186566 A1 | 9/2004 | Hindrichs et al. |
| 2004/0210244 A1 | 10/2004 | Vargas et al. |
| 2004/0225354 A1 | 11/2004 | Allen et al. |
| 2004/0260389 A1* | 12/2004 | Case et al. ............ 623/1.24 |
| 2005/0004668 A1 | 1/2005 | Aklog et al. |
| 2005/0055086 A1* | 3/2005 | Stobie ............ 623/2.1 |
| 2005/0075731 A1 | 4/2005 | Artof et al. |
| 2005/0137688 A1 | 6/2005 | Salahieh et al. |
| 2005/0137689 A1 | 6/2005 | Salahieh et al. |
| 2005/0137690 A1 | 6/2005 | Salahieh et al. |
| 2005/0137695 A1 | 6/2005 | Salahieh et al. |
| 2005/0143809 A1 | 6/2005 | Salahieh |
| 2005/0197695 A1 | 9/2005 | Stacchino et al. |
| 2005/0203549 A1 | 9/2005 | Realyvasquez |
| 2005/0216079 A1 | 9/2005 | MaCoviak |
| 2005/0234508 A1 | 10/2005 | Cummins et al. |
| 2005/0240200 A1 | 10/2005 | Bergheim |
| 2005/0251251 A1 | 11/2005 | Cribier |
| 2005/0267573 A9 | 12/2005 | Macoviak et al. |
| 2006/0047297 A1 | 3/2006 | Case |
| 2006/0178740 A1 | 8/2006 | Stacchino et al. |
| 2006/0190036 A1 | 8/2006 | Wendel et al. |
| 2006/0190038 A1 | 8/2006 | Carley et al. |
| 2006/0195184 A1 | 8/2006 | Lane et al. |
| 2006/0201519 A1 | 9/2006 | Frazier et al. |
| 2006/0241656 A1 | 10/2006 | Starksen et al. |
| 2006/0241748 A1 | 10/2006 | Lee et al. |
| 2006/0247680 A1 | 11/2006 | Amplatz et al. |
| 2006/0253191 A1 | 11/2006 | Salahieh et al. |
| 2006/0259136 A1 | 11/2006 | Nguyen et al. |
| 2006/0271171 A1* | 11/2006 | McQuinn et al. ............ 623/2.1 |
| 2007/0016288 A1 | 1/2007 | Gurskis et al. |
| 2007/0038295 A1 | 2/2007 | Case et al. |
| 2007/0043435 A1 | 2/2007 | Seguin et al. |
| 2007/0112422 A1 | 5/2007 | Dehdashtian |
| 2007/0118151 A1 | 5/2007 | Davidson |
| 2007/0162103 A1 | 7/2007 | Case et al. |
| 2007/0162107 A1 | 7/2007 | Haug et al. |
| 2007/0162111 A1 | 7/2007 | Fukamachi et al. |
| 2007/0173932 A1 | 7/2007 | Cali et al. |
| 2007/0198097 A1 | 8/2007 | Zegdi |
| 2007/0213813 A1 | 9/2007 | Von Segesser et al. |
| 2007/0225759 A1 | 9/2007 | Thommen et al. |
| 2007/0225760 A1 | 9/2007 | Moszner et al. |
| 2007/0233186 A1 | 10/2007 | Meng |
| 2007/0233237 A1 | 10/2007 | Krivoruchko |
| 2007/0239272 A1 | 10/2007 | Navia et al. |
| 2007/0255400 A1 | 11/2007 | Parravicini et al. |
| 2008/0004688 A1 | 1/2008 | Spenser et al. |
| 2008/0004697 A1 | 1/2008 | Lichtenstein et al. |
| 2008/0071363 A1 | 3/2008 | Tuval et al. |
| 2008/0071366 A1 | 3/2008 | Tuval et al. |
| 2008/0071369 A1 | 3/2008 | Tuval et al. |
| 2008/0077235 A1 | 3/2008 | Kirson |
| 2008/0086164 A1 | 4/2008 | Rowe |
| 2008/0086204 A1 | 4/2008 | Rankin |
| 2008/0167714 A1 | 7/2008 | St. Goar et al. |
| 2008/0195200 A1 | 8/2008 | Vidlund et al. |
| 2008/0208332 A1 | 8/2008 | Lamphere et al. |
| 2008/0221672 A1 | 9/2008 | Lamphere et al. |
| 2008/0243245 A1 | 10/2008 | Thambar et al. |
| 2008/0262609 A1 | 10/2008 | Gross et al. |
| 2008/0281411 A1 | 11/2008 | Berreklouw |
| 2009/0005863 A1 | 1/2009 | Goetz et al. |
| 2009/0054969 A1 | 2/2009 | Salahieh et al. |
| 2009/0099650 A1 | 4/2009 | Bolduc et al. |
| 2009/0177278 A1 | 7/2009 | Spence |
| 2009/0210052 A1 | 8/2009 | Forster et al. |
| 2009/0264994 A1 | 10/2009 | Saadat |
| 2009/0306768 A1 | 12/2009 | Quadri |
| 2009/0319037 A1 | 12/2009 | Rowe et al. |
| 2010/0023117 A1 | 1/2010 | Yoganathan et al. |
| 2010/0036479 A1 | 2/2010 | Hill et al. |
| 2010/0076548 A1 | 3/2010 | Konno |
| 2010/0114299 A1 | 5/2010 | Ben Muvhar et al. |
| 2010/0131054 A1 | 5/2010 | Tuval et al. |
| 2010/0137979 A1 | 6/2010 | Tuval et al. |
| 2010/0160958 A1 | 6/2010 | Clark |
| 2010/0161036 A1 | 6/2010 | Pintor et al. |
| 2010/0161042 A1 | 6/2010 | Maisano et al. |
| 2010/0174363 A1 | 7/2010 | Castro |
| 2010/0179643 A1 | 7/2010 | Shalev |
| 2010/0179648 A1 | 7/2010 | Richter et al. |
| 2010/0217382 A1 | 8/2010 | Chau et al. |
| 2010/0222810 A1 | 9/2010 | DeBeer et al. |
| 2010/0228285 A1 | 9/2010 | Miles et al. |
| 2010/0234940 A1 | 9/2010 | Dolan |
| 2010/0249908 A1 | 9/2010 | Chau et al. |
| 2010/0249917 A1 | 9/2010 | Zhang |
| 2010/0262232 A1 | 10/2010 | Annest |
| 2010/0280606 A1 | 11/2010 | Naor |
| 2010/0324595 A1 | 12/2010 | Linder et al. |
| 2011/0004296 A1 | 1/2011 | Lutter et al. |
| 2011/0015729 A1 | 1/2011 | Jimenez et al. |
| 2011/0015731 A1 | 1/2011 | Carpentier et al. |
| 2011/0022165 A1 | 1/2011 | Oba et al. |
| 2011/0040375 A1 | 2/2011 | Letac et al. |
| 2011/0046662 A1 | 2/2011 | Moszner et al. |
| 2011/0054466 A1 | 3/2011 | Rothstein et al. |
| 2011/0054596 A1 | 3/2011 | Taylor |
| 2011/0054598 A1 | 3/2011 | Johnson |
| 2011/0082538 A1 | 4/2011 | Dahlgren et al. |
| 2011/0087322 A1 | 4/2011 | Letac et al. |
| 2011/0093063 A1 | 4/2011 | Schreck |
| 2011/0106247 A1 | 5/2011 | Miller et al. |
| 2011/0112625 A1 | 5/2011 | Ben-Muvhar et al. |
| 2011/0112632 A1 | 5/2011 | Chau et al. |
| 2011/0118830 A1 | 5/2011 | Liddicoat et al. |
| 2011/0125257 A1 | 5/2011 | Seguin et al. |
| 2011/0125258 A1 | 5/2011 | Centola |
| 2011/0137397 A1 | 6/2011 | Chau et al. |
| 2011/0137409 A1 | 6/2011 | Yang et al. |
| 2011/0137410 A1 | 6/2011 | Hacohen |
| 2011/0166636 A1 | 7/2011 | Rowe |
| 2011/0172784 A1 | 7/2011 | Richter et al. |
| 2011/0178597 A9 | 7/2011 | Navia et al. |
| 2011/0190877 A1 | 8/2011 | Lane et al. |
| 2011/0190879 A1 | 8/2011 | Bobo et al. |
| 2011/0202076 A1 | 8/2011 | Richter |
| 2011/0208283 A1 | 8/2011 | Rust |
| 2011/0208293 A1 | 8/2011 | Tabor |
| 2011/0208298 A1 | 8/2011 | Tuval et al. |
| 2011/0213461 A1 | 9/2011 | Seguin et al. |
| 2011/0218619 A1 | 9/2011 | Benichou et al. |
| 2011/0218620 A1 | 9/2011 | Meiri et al. |
| 2011/0224785 A1 | 9/2011 | Hacohen |
| 2011/0245911 A1 | 10/2011 | Quill et al. |
| 2011/0245917 A1 | 10/2011 | Savage et al. |
| 2011/0251675 A1 | 10/2011 | Dwork |
| 2011/0251676 A1 | 10/2011 | Sweeney et al. |
| 2011/0251679 A1 | 10/2011 | Wiemeyer et al. |
| 2011/0251680 A1 | 10/2011 | Tran et al. |
| 2011/0251682 A1 | 10/2011 | Murray, III et al. |
| 2011/0251683 A1 | 10/2011 | Tabor |
| 2011/0257721 A1 | 10/2011 | Tabor |

(56) References Cited

U.S. PATENT DOCUMENTS

| | | |
|---|---|---|
| 2011/0257729 A1 | 10/2011 | Spenser et al. |
| 2011/0257736 A1 | 10/2011 | Marquez et al. |
| 2011/0257737 A1 | 10/2011 | Fogarty et al. |
| 2011/0264191 A1 | 10/2011 | Rothstein |
| 2011/0264196 A1 | 10/2011 | Savage et al. |
| 2011/0264198 A1 | 10/2011 | Murray, III et al. |
| 2011/0264199 A1 | 10/2011 | Tran et al. |
| 2011/0264200 A1 | 10/2011 | Tran et al. |
| 2011/0264201 A1 | 10/2011 | Yeung et al. |
| 2011/0264202 A1 | 10/2011 | Murray, III et al. |
| 2011/0264203 A1 | 10/2011 | Dwork et al. |
| 2011/0264206 A1 | 10/2011 | Tabor |
| 2011/0264208 A1 | 10/2011 | Duffy et al. |
| 2011/0270276 A1 | 11/2011 | Rothstein et al. |
| 2011/0271967 A1 | 11/2011 | Mortier et al. |
| 2011/0282438 A1 | 11/2011 | Drews et al. |
| 2011/0283514 A1 | 11/2011 | Fogarty et al. |
| 2011/0288634 A1 | 11/2011 | Tuval et al. |
| 2011/0301688 A1 | 12/2011 | Dolan |
| 2011/0301702 A1 | 12/2011 | Rust et al. |
| 2011/0313452 A1 | 12/2011 | Carley et al. |
| 2011/0319989 A1 | 12/2011 | Lane et al. |
| 2011/0319991 A1 | 12/2011 | Hariton et al. |
| 2012/0010694 A1 | 1/2012 | Lutter et al. |
| 2012/0022633 A1 | 1/2012 | Olson et al. |
| 2012/0022637 A1 | 1/2012 | Ben-Muvhar |
| 2012/0022639 A1 | 1/2012 | Hacohen et al. |
| 2012/0035703 A1 | 2/2012 | Lutter et al. |
| 2012/0035713 A1 | 2/2012 | Lutter et al. |
| 2012/0035722 A1 | 2/2012 | Tuval |
| 2012/0041547 A1 | 2/2012 | Duffy et al. |
| 2012/0041551 A1 | 2/2012 | Spenser et al. |
| 2012/0046738 A1 | 2/2012 | Lau et al. |
| 2012/0046742 A1 | 2/2012 | Tuval et al. |
| 2012/0053682 A1 | 3/2012 | Kovalsky et al. |
| 2012/0053688 A1 | 3/2012 | Fogarty et al. |
| 2012/0059454 A1 | 3/2012 | Millwee et al. |
| 2012/0078353 A1 | 3/2012 | Quadri et al. |
| 2012/0078357 A1 | 3/2012 | Conklin |
| 2012/0083832 A1 | 4/2012 | Delaloye et al. |
| 2012/0083839 A1 | 4/2012 | Letac et al. |
| 2012/0083879 A1 | 4/2012 | Eberhardt et al. |
| 2012/0089223 A1 | 4/2012 | Nguyen et al. |
| 2012/0101570 A1 | 4/2012 | Tuval et al. |
| 2012/0101572 A1 | 4/2012 | Kovalsky et al. |
| 2012/0123530 A1 | 5/2012 | Carpentier et al. |
| 2012/0136434 A1 | 5/2012 | Carpentier et al. |
| 2012/0150218 A1 | 6/2012 | Sandgren et al. |
| 2012/0197292 A1 | 8/2012 | Chin-Chen et al. |
| 2012/0283824 A1 | 11/2012 | Lutter et al. |
| 2012/0290062 A1 | 11/2012 | McNamara et al. |
| 2012/0310328 A1 | 12/2012 | Olson et al. |
| 2012/0323316 A1 | 12/2012 | Chau et al. |
| 2013/0035759 A1 | 2/2013 | Gross et al. |
| 2013/0261737 A1 | 10/2013 | Costello |
| 2013/0304197 A1 | 11/2013 | Buchbinder et al. |
| 2013/0325114 A1 | 12/2013 | McLean et al. |
| 2014/0005778 A1 | 1/2014 | Buchbinder et al. |
| 2014/0052237 A1 | 2/2014 | Lane et al. |

FOREIGN PATENT DOCUMENTS

| | | |
|---|---|---|
| WO | 00/47139 A1 | 8/2000 |
| WO | 01/62189 A1 | 8/2001 |
| WO | 2006/054930 A1 | 5/2006 |
| WO | 2008/013915 A3 | 1/2008 |
| WO | 2009/033469 A1 | 3/2009 |
| WO | 2009/053497 A1 | 4/2009 |
| WO | 2010/006627 A1 | 1/2010 |
| WO | 2010/073246 A2 | 7/2010 |
| WO | 2011/106137 A1 | 9/2011 |
| WO | 2011/111047 A2 | 9/2011 |
| WO | 2011/143263 A2 | 11/2011 |
| WO | 2012/011108 A2 | 1/2012 |
| WO | 2013/021374 A2 | 2/2013 |
| WO | 2013/021375 A2 | 2/2013 |
| WO | 2013/078497 A1 | 6/2013 |

OTHER PUBLICATIONS

Alexander Geha et al; "Replacement of Degenerated Mitral and Aortic Bioprostheses Without Explanation", Ann. Thoracic Surgery 2001; 72:1509-1514; Accepted for publication Jun. 1, 2001.

John G. Webb, et al; "Transcatheter Valve-in-Valve Implantation for Failed Bioprosthetic Heart Valves", Circulation 2010; 121; 1848-1857; originally published online Apr. 12, 2010.

Alexander S. Geha, et al; "Replacement of Degenerated Mitral and Aortic Bioprostheses Without Explanation", The Annals of thoracic Surgery, vol. 72, Issue 5, Nov. 2001, pp. 1509-1514.

F. Langer, et al; "Ring plus String: Papillary muscle repositioning as an adjunctive repair technique for ischemic mitral regurgitation", The Journal of Thoracic and Cardiovascular Surgery, (Exact Date Not Given), 133, pp. 247-249.

F. Langer, et al; "Ring+String: Successful Repair Technique for Ischemic Mitral Regurgitation With Severe Leaflet Tethering".

John G. Webb, et al; "Transcatheter Valve-In-Valve Implantation for Failed Bioprosthetic Heart Valves", Circulation, Journal of The American Heart Association, Apr. 27, 2010, vol. 121, No. 16, 11 pages.

Josef Jansen, et al; "Detachable shape-memory sewing ring for heart valves", Artificial Organs, vol. 16, Issue 3, pp. 294-297, Jun. 1992.

USPTO NFOA mailed May 29, 2012 in connection with U.S. Appl. No. 12/840,463.

ISR & Written Opinion dated Dec. 5, 2011 issued during prosecution of PCT/IL11/00582.

ISR & Written opinion dated Feb. 6, 2013; PCT/IL12/00292.

ISR & Written Opinion dated Feb. 6, 2013; PCT/IL12/00293.

USPTO NFOA dated Nov. 28, 2012 in connection with U.S. Appl. No. 12/961,721.

USPTO NFOA dated Dec. 31, 2012 in connection with U.S. Appl. No. 13/044,694.

USPTO NFOA dated Feb. 6, 2013 in connection with U.S. Appl. No. 13/412,814.

USPTO FOA dated Feb. 15, 2013 in connection with U.S. Appl. No. 12/840,463.

USPTO NFOA dated Sep. 12, 2013 in connection with U.S. Appl. No. 13/412,814.

An Office Action dated Jul. 18, 2013, which issued during the prosecution of U.S. Appl. No. 13/044,694.

An Office Action dated Jul. 23, 2013, which issued during the prosecution of U.S. Appl. No. 12/961,721.

International Search Report and Written Opinion dated Sep. 4, 2014 PCT/IL2014/050087.

USPTO NFOA dated Sep. 19, 2014 in connection with U.S. Appl. No. 13/044,694.

Dominique Himbert MD; "Mitral Regurgitation and Stenosis from Bioprosthesis and Annuloplasty Failure: Transcather Approaches and Outcomes", Presentation made Oct. 28, 2013, 24 pages.

Invitation to Pay Additional Fees dated Jun. 12, 2014 issued during prosecution of PCT/IL2014/050087.

USPTO NFOA dated Jun. 17, 2014 in connection with U.S. Appl. No. 12/961,721.

USPTO NFOA dated Jul. 2, 2014 in connection with U.S. Appl. No. 13/811,308.

USPTO FOA dated May 23, 2014 in connection with U.S. Appl. No. 13/412,814.

* cited by examiner

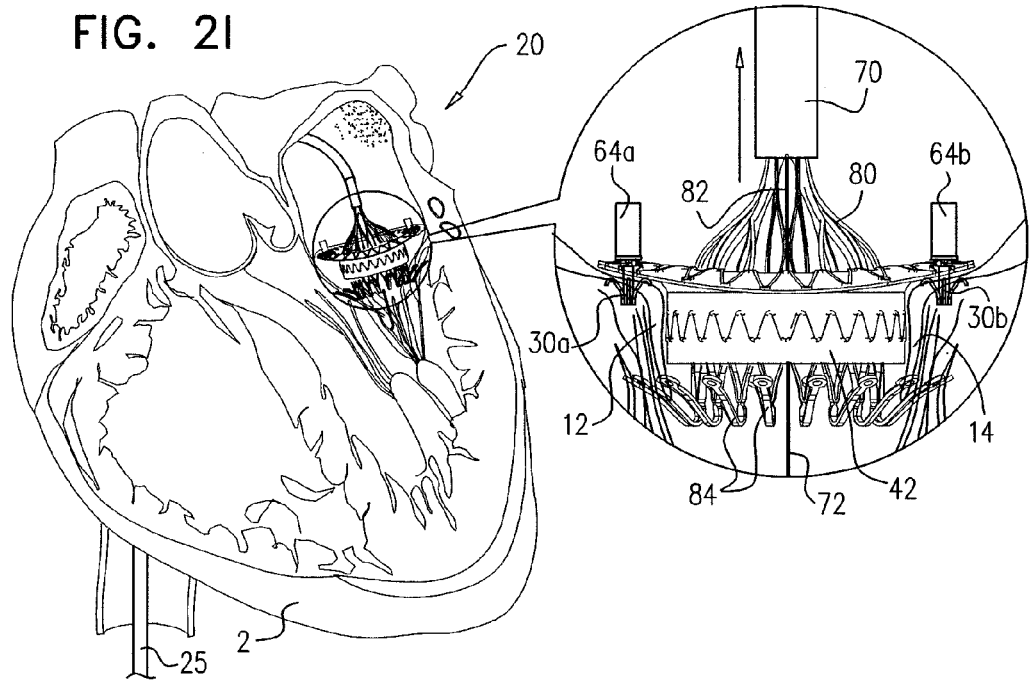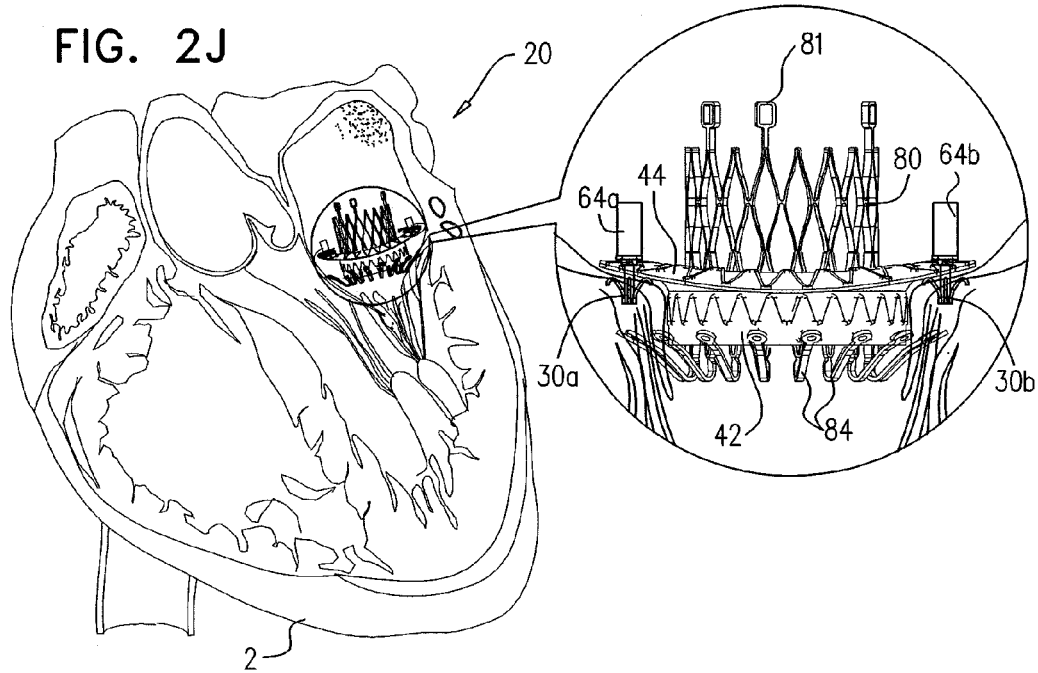

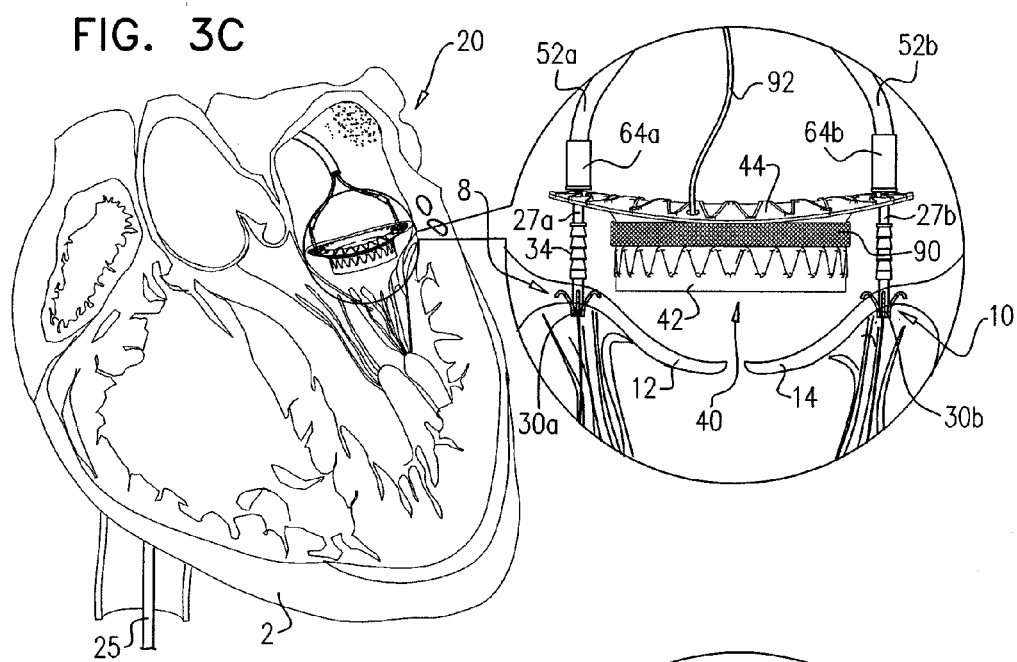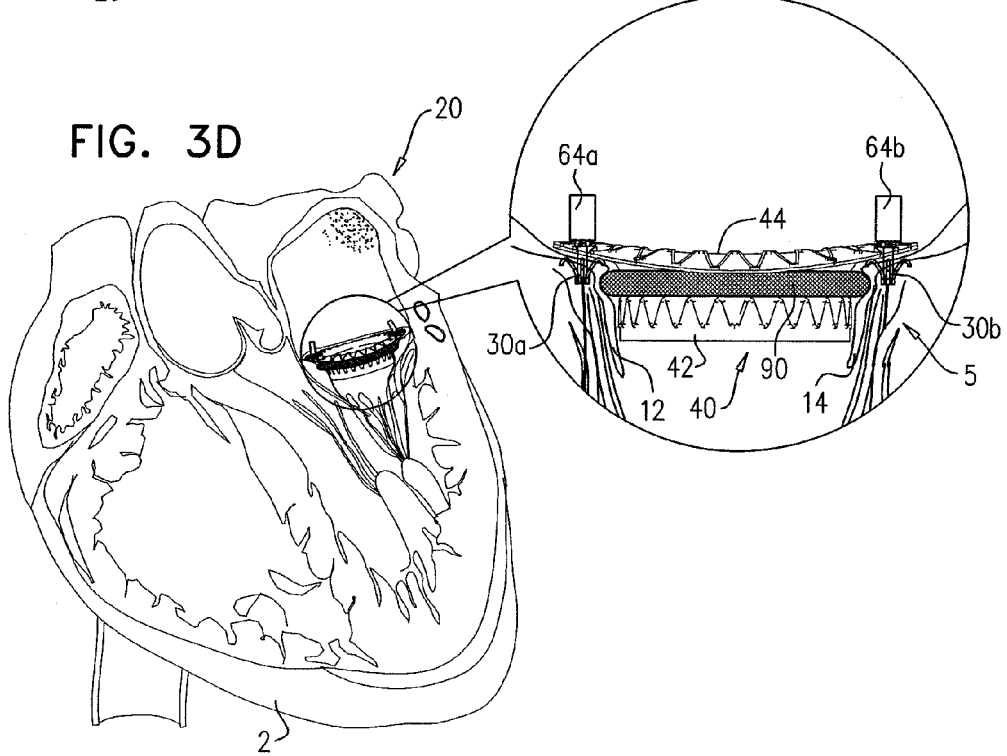

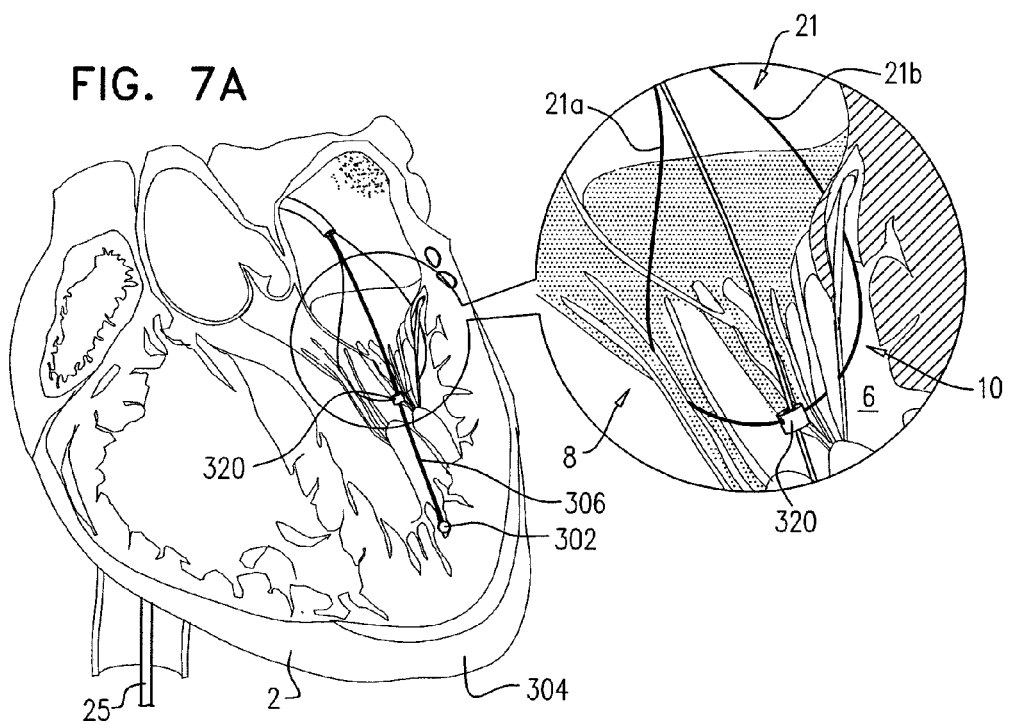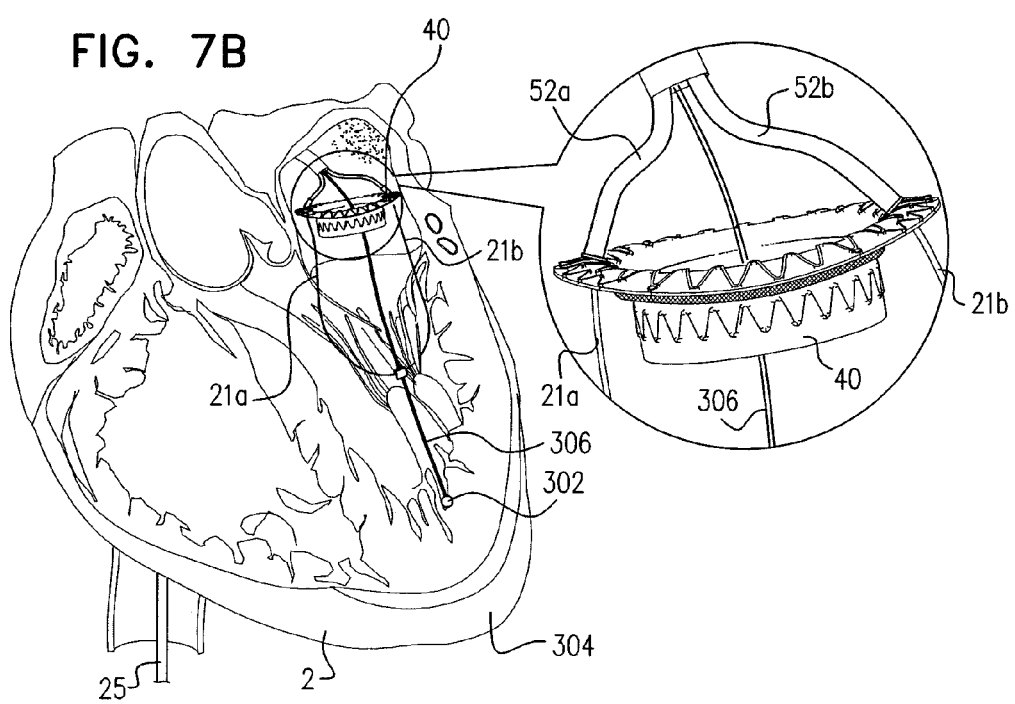

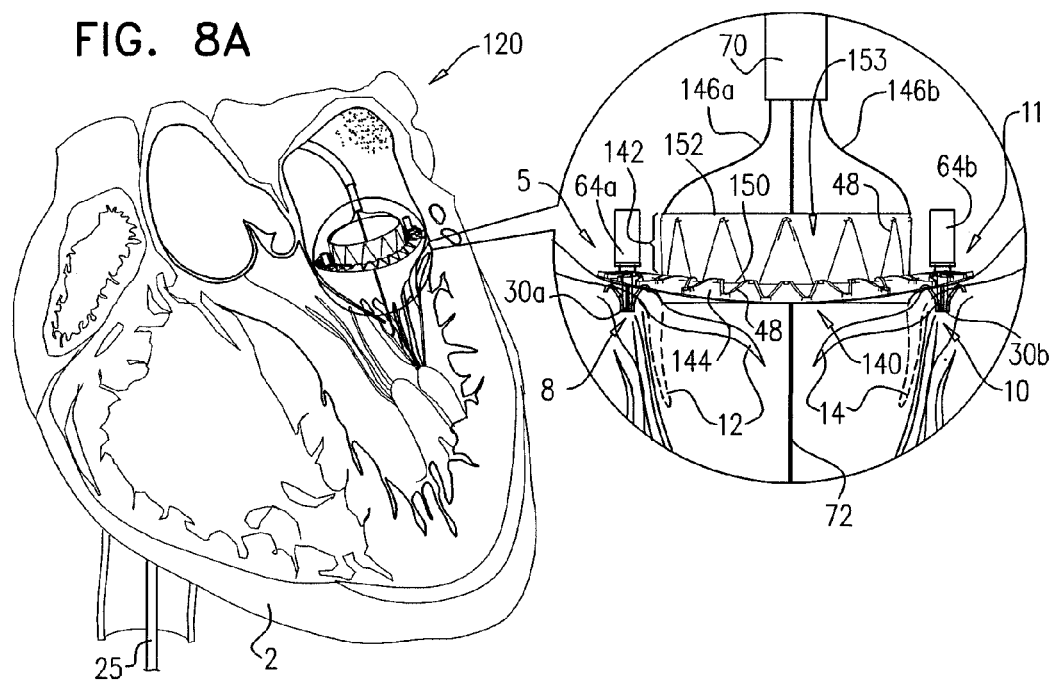
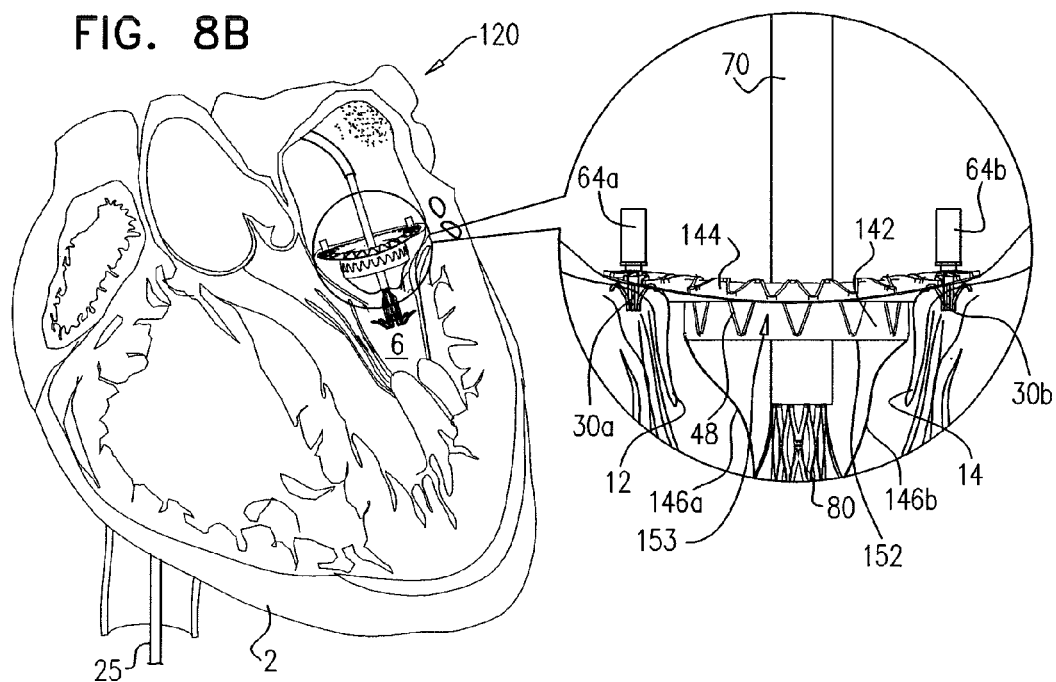

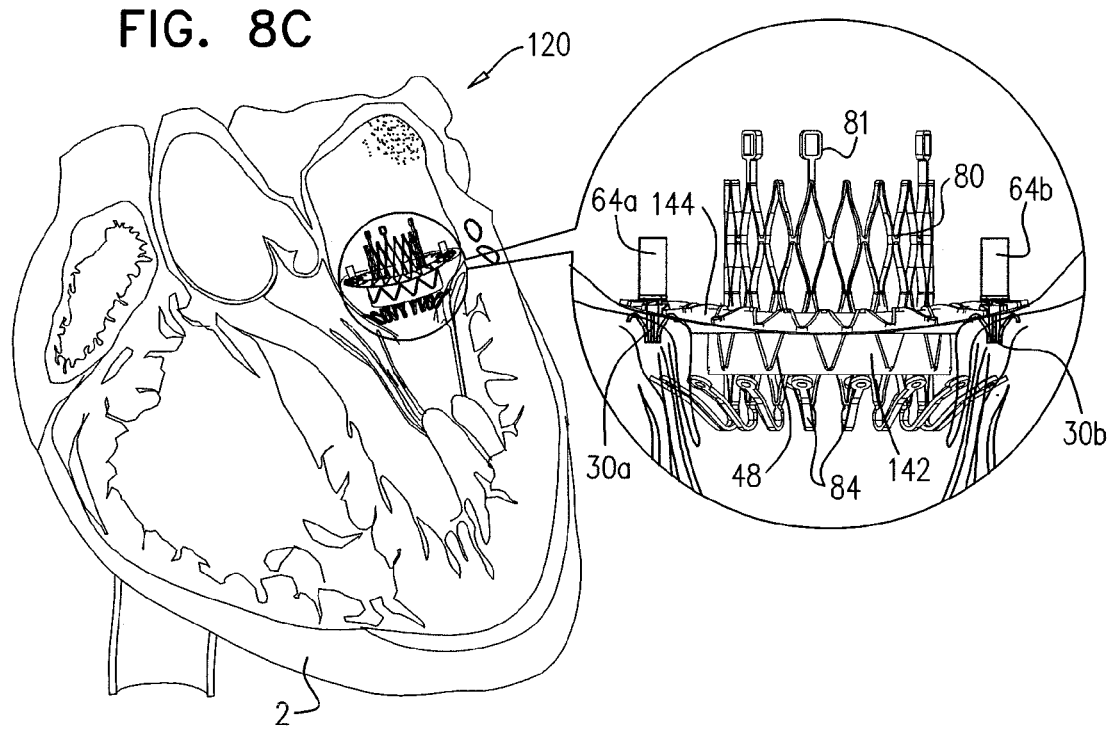

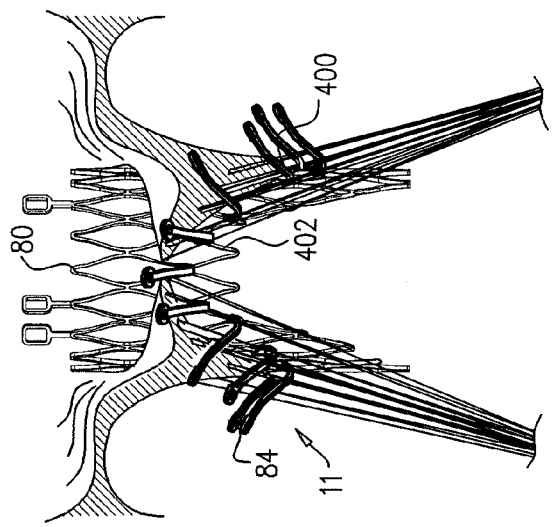
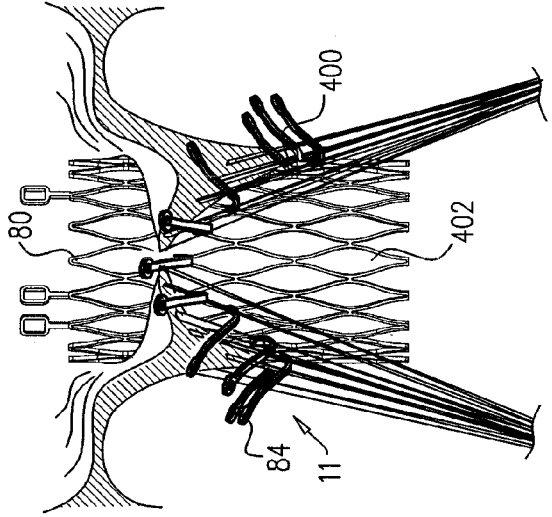
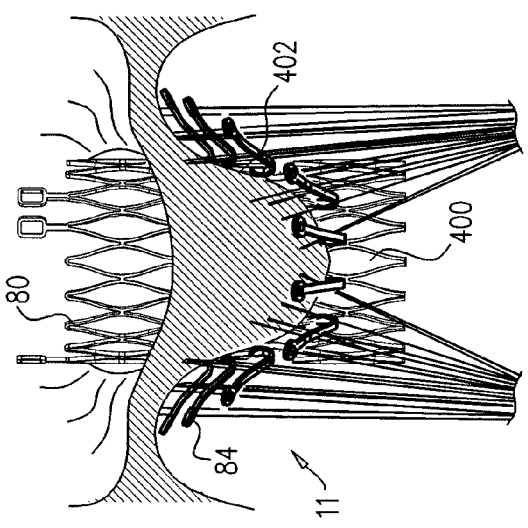

TECHNIQUES FOR PERCUTANEOUS MITRAL VALVE REPLACEMENT AND SEALING

CROSS-REFERENCES TO RELATED APPLICATIONS

The present application is a continuation-in-part of U.S. Ser. No. 12/840,463 to Hacohen, filed Jul. 21, 2010, entitled "Guide wires with commissural anchors to advance a prosthetic valve," which published as US 2012/0022639, and which is incorporated herein by reference.

FIELD OF THE INVENTION

Embodiments of the present invention relate in general to valve replacement. More specifically, embodiments of the present invention relate to prosthetic valves for replacement of an atrioventricular valve.

BACKGROUND

Ischemic heart disease causes regurgitation of a heart valve by the combination of ischemic dysfunction of the papillary muscles, and the dilatation of the ventricle that is present in ischemic heart disease, with the subsequent displacement of the papillary muscles and the dilatation of the valve annulus.

Dilation of the annulus of the valve prevents the valve leaflets from fully coapting when the valve is closed. Regurgitation of blood from the ventricle into the atrium results in increased total stroke volume and decreased cardiac output, and ultimate weakening of the ventricle secondary to a volume overload and a pressure overload of the atrium.

SUMMARY

For some applications of the present invention, one or more guide members (e.g., wires, sutures, or strings) is configured to be anchored to respective commissures of a native atrioventricular valve of a patient, and each guide member facilitates the advancement therealong of respective commissural anchors. The commissural anchors are shaped so as to define a plurality of barbs or prongs which are expandable to restrict proximal movement of the anchors following their deployment. The guide members facilitate advancement of a collapsible prosthetic valve support (e.g., a skirt) which serves as a base for and receives a collapsible prosthetic mitral valve which is subsequently coupled to the support. The support comprises a proximal annular element, or ring, and a distal cylindrical element. The cylindrical element is configured to push aside and press against the native leaflets of the native valve, and the proximal annular element is shaped so as to define one or more holes for sliding the valve support along the one or more guide members. The proximal annular element is configured to be positioned along the annulus of the native valve.

The collapsible prosthetic valve is configured for implantation in and/or at least partial replacement (e.g., full replacement) of the native atrioventricular valve of the patient, such as a native mitral valve or a native tricuspid valve. The valve support and the prosthetic valve are configured to assume collapsed states for minimally-invasive delivery to the diseased native valve, such as by percutaneous or transluminal delivery using one or more catheters. For some applications, the valve support and the prosthetic valve are implanted during an open-heart procedure.

The prosthetic valve support is shaped so as to define a downstream skirt. The downstream skirt is configured to be placed at native valve, such that the downstream skirt passes through the orifice of the native valve and extends toward, and, typically partially into, a ventricle. The downstream skirt typically additionally pushes aside and presses against the native leaflets of the native valve, which are left in place during and after implantation of the prosthetic valve support and/or the prosthetic valve.

The proximal annular element has upper and lower surfaces. For some applications of the present invention, one or more, e.g., a plurality of, tissue anchors are coupled to the lower surface and facilitate anchoring of the proximal annular element to the annulus of the native valve. For some applications, the one or more anchors comprise at least first and second commissural anchors that are configured to be implanted at or in the vicinity of the commissures of the native valve.

The cylindrical element of the valve support has first and second ends and a cylindrical body disposed between the first and second ends. The first end of the cylindrical element is coupled to the annular element while the second end defines a free end of the cylindrical element. For some applications of the present invention, the cylindrical element of the valve support is invertible such that (1) during a first period, the second end and the cylindrical body of the cylindrical element are disposed above the annular element (e.g., in the atrium of the heart), and (2) during a second period, the second end and the cylindrical body of the cylindrical element are disposed below the annular element (e.g., in the ventricle of the heart).

For some applications, techniques are applied to facilitate sealing of the interface between the valve support and the native valve, and/or the interface between the prosthetic valve and the native valve. For example, a sealing balloon may be placed on a valve-facing, lower side of the annular element of the valve support, the sealing balloon being configured to be inflated such that the balloon seals the interface between the valve support and the native valve. Alternatively or additionally, commissural helices are wrapped around chordae tendineae of the patient in order to facilitate sealing of the valve commissures around the valve support and/or around the valve. Further alternatively or additionally, the valve commissures are grasped by grasping elements that act in order to facilitate sealing of the commissures around the valve support and/or around the valve. For some applications, one or more of the aforementioned sealing elements facilitates anchoring of the prosthetic valve to the native valve in addition to facilitating sealing.

For some applications, the prosthetic valve comprises a wire frame, and a sealing material (such as latex) is disposed on the outer surface of the wire frame so as to form webbing between at least some of the struts of the wire frame, and to provide sealing between the wire frame and the native valve.

For some applications, an invertible prosthetic valve support is used to support a prosthetic valve. Typically, a sealing element is disposed circumferentially around a surface of the invertible prosthetic valve support that is initially an inner surface of the invertible prosthetic valve support. The invertible prosthetic valve support is anchored to the native valve, and is subsequently inverted. Subsequent to the inversion of the invertible prosthetic valve support, the sealing element is disposed on the outer surface of the invertible prosthetic valve support and acts to seal the interface between the outer surface and the native valve.

There is therefore provided, in accordance with some applications of the present invention, apparatus, including:

one or more valve support guide members configured to be delivered to one or more commissures of a native atrioventricular valve of a patient;

a prosthetic valve support configured to be advanced toward the native valve along the one or more valve support guide members and placed at the native valve;

a prosthetic valve configured to be coupled to the valve support; and one or more sealing elements configured to facilitate sealing of an interface between the prosthetic valve support and the native valve.

For some applications, the sealing element includes a balloon disposed circumferentially around an outer surface of the prosthetic valve support.

For some applications, the sealing element includes one or more helices that are configured to facilitate sealing of commissures of the native valve with respect to the valve support by being wrapped around chordae tendineae of the native valve.

For some applications, the sealing element includes grasping elements that are configured to facilitate sealing of commissures of the native valve with respect to the valve support by grasping the commissures.

For some applications, the sealing element is configured to facilitate anchoring of the support to the native valve.

For some applications, the valve support is collapsible for transcatheter delivery and expandable to contact the native atrioventricular valve.

For some applications, the prosthetic valve includes two or more prosthetic leaflets.

For some applications, the native atrioventricular valve includes a mitral valve, and the prosthetic valve includes three prosthetic leaflets.

For some applications, the valve support guide members are removable from the patient following coupling of the prosthetic valve to the valve support.

For some applications, the valve support is shaped so as to define a distal portion which is configured to push aside, at least in part, native leaflets of the valve of the patient.

For some applications, the valve support is shaped so as to define one or more holes, the one or more holes being configured to facilitate slidable passage therethrough of a respective one of the one or more valve support guide members.

For some applications, the one or more valve support guide members includes one valve support guide member that is looped through first and second commissures of the atrioventricular valve in a manner in which a looped portion of the valve support guide member is disposed in a ventricle of the patient and first and second free ends of the valve support guide member are accessible from a site outside a body of the patient.

For some applications, the apparatus further includes:

a guide wire configured to be advanced, via the native atrioventricular valve, into a ventricle of the patient, and coupled to an inner wall of the patient's ventricle; and a valve support guide member tube coupled to the guide wire, and a distal portion of the valve support guide member is configured to loop through the valve support guide member tube, such that, in response to the valve support guide member being pushed distally, portions of the valve support guide member are pushed to respective commissures of the native valve.

For some applications, the prosthetic valve is shaped so as to define one or more protrusions configured to ensnare one or more native leaflets of the native valve of the patient.

For some applications, the protrusions are disposed in a sinusoidal configuration such that the protrusions conform with a saddle shape of the patient's native annulus.

For some applications, the protrusions are configured to prevent the native leaflets from interfering with a left ventricular outflow tract of the patient, by sandwiching the leaflets between the protrusions and the prosthetic valve support.

For some applications, the valve support includes:

a first end that is configured to be placed on an atrial side of a native atrioventricular valve of a patient; and a second end that is configured, during a first period, to be disposed inside the patient's atrium, above the first end of the valve support, the valve support being at least partially invertible in a manner in which, during a second period, the second end of the valve support is disposed at least partially inside a ventricle of the patient, below the first end of the valve support.

For some applications, the valve support includes an annular element and a generally cylindrical element coupled to the annular element, the generally cylindrical element being configured to push aside native leaflets of the native valve, and the cylindrical element has first and second ends and a cylindrical body that is disposed between the first and second ends.

For some applications, the sealing element includes a balloon disposed underneath the annular element and configured to facilitate sealing of an interface between the annular element and the native valve.

For some applications, the apparatus further includes one or more prosthetic valve guide members, the prosthetic valve guide members being configured to facilitate advancement of the prosthetic valve therealong and toward the valve support.

For some applications:

the first end of the cylindrical element is coupled to the annular element, during a first period, the second end of the cylindrical element is disposed above the annular element in a manner in which the body of the cylindrical element is disposed above the annular element, and the cylindrical element is invertible in a manner in which, during a second period, the second end of the cylindrical element is disposed below the annular element and the body of the cylindrical element is disposed below the annular element.

For some applications:

during the first period, the second end of the cylindrical element is disposed in an atrium of a heart of the patient and the annular element is positioned along an annulus of the native valve, the prosthetic valve is advanceable along the one or more prosthetic valve guide members into a ventricle of the heart of the patient, and in response to advancement of the prosthetic valve into the ventricle, the one or more prosthetic valve guide members are pulled into the ventricle and pull the second end and the body of the cylindrical element into the ventricle to invert the cylindrical element.

There is further provided, in accordance with some applications of the present invention, apparatus, including:

a prosthetic valve support configured to be advanced toward a native atrioventricular valve of a patient and placed at the native valve;

a prosthetic valve configured to be coupled to the valve support, the prosthetic valve being shaped so as to define first and second sets of one or more protrusions, each set of protrusions configured to ensnare a respective native leaflet of the native valve of the patient, the first set of protrusions being disposed within a first circumferential arc with respect to a longitudinal axis of the prosthetic valve, on a first side of a distal end of the prosthetic valve, the second set of protrusions being disposed within a second circumferential arc with respect to the longitudinal axis of the prosthetic valve, on a second side of the distal end of the prosthetic valve, the first and second sets being disposed so as to provide first and second gaps therebetween at the distal end of the prosthetic valve, at least one of the gaps having a circumferential arc of at least 20 degrees; and one or more valve guide members configured to be delivered to one or more commissures of the native valve, and to guide the valve such that the first and second circumferential arcs are aligned with respective leaflets of the native valve and such that the first and second gaps are aligned with respective commissures of the native valve.

For some applications, the at least one of the gaps has a circumferential arc of at least 60 degrees.

For some applications, the first circumferential arc defines an angle of between 25 degrees and 90 degrees about the longitudinal axis of the prosthetic valve.

For some applications, the second circumferential arc defines an angle of between 25 degrees and 90 degrees about the longitudinal axis of the prosthetic valve.

For some applications, the first circumferential arc defines an angle of between 45 degrees and 75 degrees about the longitudinal axis of the prosthetic valve.

For some applications, the second circumferential arc defines an angle of between 45 degrees and 75 degrees about the longitudinal axis of the prosthetic valve.

There is additionally provided, in accordance with some applications of the present invention, a method, including:

determining an area defined by an annulus of a native atrioventricular valve of a patient;

selecting a prosthetic valve to be placed in the native valve by determining that the valve defines a cross-sectional area that is less than 90% of the area defined by the annulus; and deploying the prosthetic valve at the native valve, the selecting of the prosthetic valve facilitating sealing of the native valve with respect to the prosthetic valve by facilitating closing of leaflets of the native valve around the prosthetic valve, upon deployment of the prosthetic valve.

For some applications, selecting the prosthetic valve includes selecting a prosthetic valve having a material disposed on an outer surface thereof.

For some applications, selecting the prosthetic valve includes selecting a prosthetic valve having a material that prevents tissue growth disposed on an outer surface thereof.

For some applications, selecting the prosthetic valve includes selecting a prosthetic valve having a material that promotes tissue growth disposed on an outer surface thereof.

For some applications, selecting the prosthetic valve to be placed in the native valve includes determining that the valve defines a cross-sectional area that is less than 80% of the area defined by the annulus.

For some applications, selecting the prosthetic valve to be placed in the native valve includes determining that the valve defines a cross-sectional area that is less than 60% of the area defined by the annulus.

There is further provided, in accordance with some applications of the present invention, apparatus including:

a valve support for receiving a prosthetic valve, the valve support including:

a first end that is configured to be placed on an atrial side of a native atrioventricular valve of a patient; and a second end that is configured, during a first period, to be disposed inside the patient's atrium, above the first end of the valve support, the valve support being at least partially invertible in a manner in which, during a second period, the second end of the cylindrical element is disposed at least partially inside a ventricle of the patient, below the first end of the valve support.

For some applications, the valve support includes a flexible wireframe covered by a fabric.

For some applications, the valve support is collapsible for transcatheter delivery and expandable to contact the native atrioventricular valve.

For some applications, the valve support defines a surface that is an inner surface of the valve support during the first period, and an outer surface of the valve support during the second period, and the apparatus further includes a sealing material that is disposed on the surface, such that during the second period the sealing material facilitates sealing between the valve support and the native valve.

For some applications, the first end includes a coupling element configured to couple the valve support to tissue of the native valve on the atrial side of the native valve.

For some applications, the first end is shaped to define barbs that are configured to couple the valve support to tissue of the native valve on the atrial side of the native valve For some applications, the valve support includes:

an annular element configured to be positioned along a native annulus of the native atrioventricular valve; and a flexible generally cylindrical element configured to be positioned in the native atrioventricular valve of the patient and to push aside native leaflets of the native valve, the first end of the cylindrical element defining the first end of the valve support, and the first end of the cylindrical element being coupled to the annular element.

For some applications, the apparatus further includes one or more valve support guide members configured to be delivered to one or more commissures of the native atrioventricular valve of the patient, and the one or more valve support guide members are configured to facilitate advancement of the valve support toward the native valve.

For some applications, the valve support is shaped so as to define one or more holes, the one or more holes configured to facilitate slidable passage therethrough of a respective one of the one or more valve support guide members.

For some applications, the one or more valve support guide members includes one valve support guide member that is looped through first and second commissures of the atrioventricular valve in a manner in which a looped portion of the valve support guide member is disposed in a ventricle of the patient and first and second free ends of the valve support guide member are accessible from a site outside a body of the patient.

For some applications, the apparatus further includes:

a guide wire configured to be advanced, via the native atrioventricular valve, into a ventricle of the patient, and coupled to an inner wall of the patient's ventricle; and a valve support guide member tube coupled to the guide wire, and a distal portion of the valve support guide member is configured to loop through the valve support guide member tube, such that, in response to the valve support guide member being pushed distally, portions of the valve support guide member are pushed to respective commissures of the native valve.

For some applications, the apparatus further includes one or more prosthetic valve guide members reversibly couplable to the cylindrical element in a vicinity of the second end of the cylindrical element, the prosthetic valve guide members being configured to facilitate advancement of the prosthetic valve therealong and toward the valve support.

For some applications, the apparatus further includes the prosthetic valve, and the prosthetic valve is couplable to the valve support.

For some applications:

during the first period, the second end of the cylindrical element is disposed in an atrium of a heart of the patient and the annular element is positioned along an annulus of the native valve, the prosthetic valve is advanceable along the one or more prosthetic valve guide members into a ventricle of the heart of the patient, and in response to advancement of the prosthetic valve into the ventricle, the one or more prosthetic valve guide members are pulled into the ventricle and pull the second end of the cylindrical element into the ventricle to invert the cylindrical element.

For some applications, the apparatus further includes one or more sealing elements configured to facilitate sealing of an interface between the prosthetic valve support and the native valve.

For some applications, the sealing element includes a balloon disposed circumferentially around a surface of the prosthetic valve support.

For some applications, the sealing element includes one or more helices that are configured to facilitate sealing of commissures of the native valve with respect to the valve support by being wrapped around chordae tendineae of the native valve.

For some applications, the sealing element includes grasping elements that are configured to facilitate sealing of commissures of the native valve with respect to the valve support by grasping the commissures.

For some applications, the sealing element is configured to facilitate anchoring of the support to the native valve.

For some applications, the apparatus further includes the prosthetic valve, and the prosthetic valve is couplable to the valve support.

For some applications, the prosthetic valve is collapsible for transcatheter delivery and expandable when exposed from within a delivery catheter.

For some applications, the prosthetic valve includes two or more prosthetic leaflets.

For some applications, the native atrioventricular valve includes a mitral valve, and the prosthetic valve includes three prosthetic leaflets.

For some applications, the prosthetic valve is shaped so as to define one or more protrusions configured to ensnare one or more native leaflets of the native valve of the patient.

For some applications, the protrusions are disposed in a sinusoidal configuration such that the protrusions conform with a saddle shape of the patient's native annulus.

For some applications, the protrusions are configured to prevent the native leaflets from interfering with a left ventricular outflow tract of the patient, by sandwiching the leaflets between the protrusions and the prosthetic valve support.

There is further provided, in accordance with some applications of the present invention, apparatus, including:

a guide wire configured to be advanced into a patient's ventricle via a native atrioventricular valve of the patient, and coupled to an inner wall of the patient's ventricle;

a valve support guide member tube coupled to the guide wire;

a valve support guide member, a distal portion of the valve support guide member looping through the valve support guide member tube, such that, in response to the valve support guide member being pushed distally, portions of the valve support guide member are pushed to respective commissures of the native valve;

a prosthetic valve support configured to be advanced toward the commissures of the native valve along the valve support guide member portions; and a prosthetic valve configured to be coupled to the valve support.

For some applications, first and second free ends of the valve support guide member are accessible from a site outside a body of the patient.

For some applications, the valve support includes:

an annular element configured to be positioned along a native annulus of the native atrioventricular valve; and a generally cylindrical element configured to be positioned in the native atrioventricular valve of the patient and to push aside native leaflets of the native valve, the cylindrical element being coupled to the annular element, at a first end of the cylindrical element.

For some applications, the valve support is shaped so as to define one or more holes, the one or more holes configured to facilitate slidable passage therethrough of respective portions of the portions of the valve support guide member.

For some applications, the guide member is configured to facilitate advancement of the prosthetic valve therealong and toward the valve support.

For some applications, the prosthetic valve is collapsible for transcatheter delivery and expandable when exposed from within a delivery catheter.

For some applications, the prosthetic valve includes two or more prosthetic leaflets.

For some applications, the native atrioventricular valve includes a mitral valve, and the prosthetic valve includes three prosthetic leaflets.

For some applications, the guide member is removable from the patient following the coupling of the prosthetic valve to the valve support.

For some applications, the prosthetic valve is shaped so as to define one or more protrusions configured to ensnare one or more native leaflets of the native valve of the patient.

For some applications, the protrusions are disposed in a sinusoidal configuration such that the protrusions conform with a saddle shape of the patient's native annulus.

For some applications, the protrusions are configured to prevent the native leaflets from interfering with a left ventricular outflow tract of the patient, by sandwiching the leaflets between the protrusions and the prosthetic valve support.

For some applications, the apparatus further includes one or more sealing elements configured to facilitate sealing of an interface between the prosthetic valve support and the native valve.

For some applications, the sealing element includes a balloon disposed circumferentially around a surface of the prosthetic valve support.

For some applications, the sealing element includes one or more helices that are configured to facilitate sealing of commissures of the native valve with respect to the valve support by being wrapped around chordae tendineae of the native valve.

For some applications, the sealing element includes grasping elements that are configured to facilitate sealing of commissures of the native valve with respect to the valve support by grasping the commissures.

For some applications, the sealing element is configured to facilitate anchoring of the support to the native valve.

There is additionally provided, in accordance with some applications of the present invention, apparatus, including:

one or more valve guide members configured to be delivered to one or more commissures of a native atrioventricular valve of a patient;

a prosthetic valve configured to be advanced to be advanced toward the native valve along the one or more valve guide members and placed at the native valve at least the one or more commissures; and one or more proximally-facing grasping elements that are configured to facilitate sealing of commissures of the native valve with respect to the valve by:

being inserted into a ventricle of the patient; and being pulled proximally and being closed around tissue in a vicinity of the commissures.

For some applications, the grasping elements include two surfaces that are hingedly coupled to one another, and that are configured to facilitate the sealing of the commissures of the native valve with respect to the prosthetic valve by being closed about the hinge with respect to one another.

There is further provided, in accordance with some applications of the present invention, a method, including:

advancing one or more valve support guide members toward one or more commissures of a native atrioventricular valve of a patient;

placing a prosthetic valve support at the native atrioventricular valve by advancing the valve support along the one or more valve support guide members;

coupling a prosthetic valve to the prosthetic valve support; and facilitating sealing of an interface between the prosthetic valve support and the native valve by deploying a sealing element in a vicinity of the interface.

There is additionally provided, in accordance with some applications of the present invention, a method including:

placing a first end of a prosthetic valve support on an atrial side of a native atrioventricular valve of a patient, such that a second end of the valve support is disposed, during a first period, inside the patient's atrium, above the first end of the valve support; and subsequent to the placing of the valve support, inverting at least a portion of the valve support such that, during a second period, the second end of the valve support is disposed at least partially inside a ventricle of the patient, below the first end of the valve support.

There is additionally provided, in accordance with some applications of the present invention, a method, including:

advancing a guide wire, via a native atrioventricular valve, into a ventricle of the patient, a valve support guide member tube being coupled to the guide wire;

coupling a distal end of the guide wire to an inner wall of the patient's ventricle; and causing portions of a valve support guide member to be pushed to respective commissures of the native valve, by pushing the guide member distally, a distal portion of the valve support guide member looping through the valve support guide member tube;

advancing a prosthetic valve support toward the commissures of the native valve along the valve support guide member portions; and coupling a prosthetic valve to the valve support.

There is further provided, in accordance with some applications of the present invention, a method, including:

advancing one or more valve guide members toward one or more commissures of a native atrioventricular valve of a patient;

placing a prosthetic valve at the native atrioventricular valve by advancing the valve along the one or more valve guide members; and facilitating sealing of commissures of the native valve with respect to the valve by:

inserting into a ventricle of the patient one or more grasping elements that are coupled to the prosthetic valve;

pulling the grasping elements proximally; and closing the grasping elements around tissue in a vicinity of the commissures.

The present invention will be more fully understood from the following detailed description of embodiments thereof, taken together with the drawings, in which:

BRIEF DESCRIPTION OF THE DRAWINGS

FIGS. 2G-K are schematic illustrations of the advancement of a prosthetic valve and the coupling of the prosthetic valve to the valve support, in accordance with some applications of the present invention;

FIGS. 3C-D are schematic illustrations of locking of the prosthetic valve support at the native valve, the valve support including the sealing balloon, in accordance with some applications of the present invention;

FIGS. 7A-F are schematic illustrations of a guide wire delivery system, in accordance with some applications of the present invention;

FIGS. 8A-C are schematic illustrations of a valve support that has a cylindrical element that is invertible, in accordance with some applications of the present invention;

FIGS. 12A-C are schematic illustrations of a prosthetic valve that defines distal protrusions that are disposed sinusoidally around the circumference of the valve, in accordance with some applications of the present invention.

DETAILED DESCRIPTION OF THE EMBODIMENTS

Figure 1A:
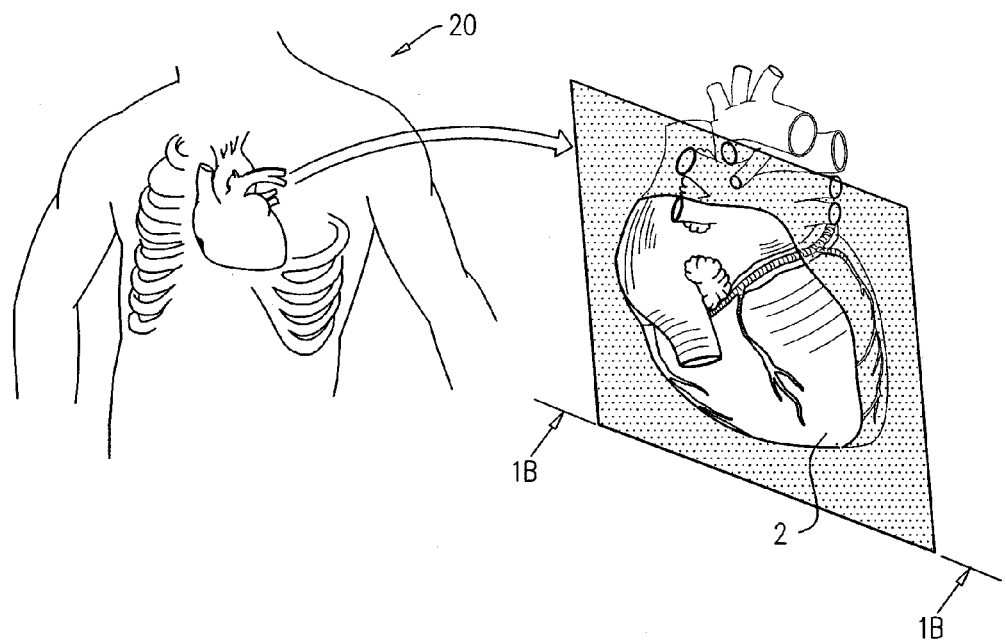
FIGS. 1A-B are schematic illustrations of advancement of one or more guide members toward respective commissures of a mitral valve, in accordance with some applications of the present invention.
Figure 1B:
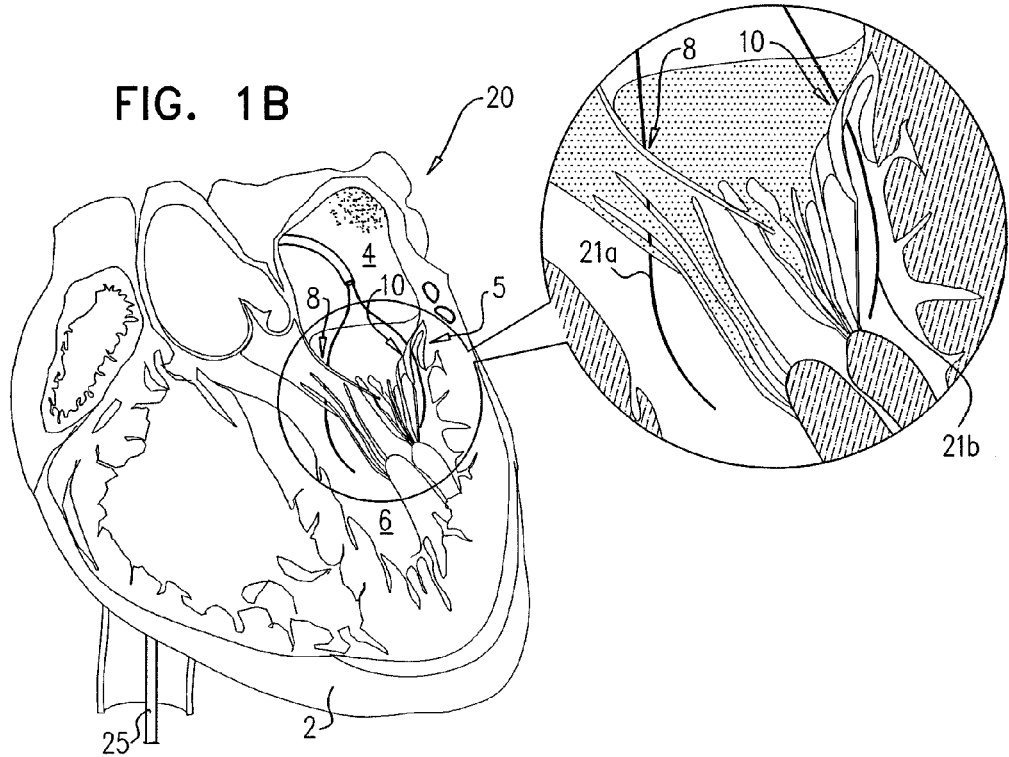
Figure 1C:
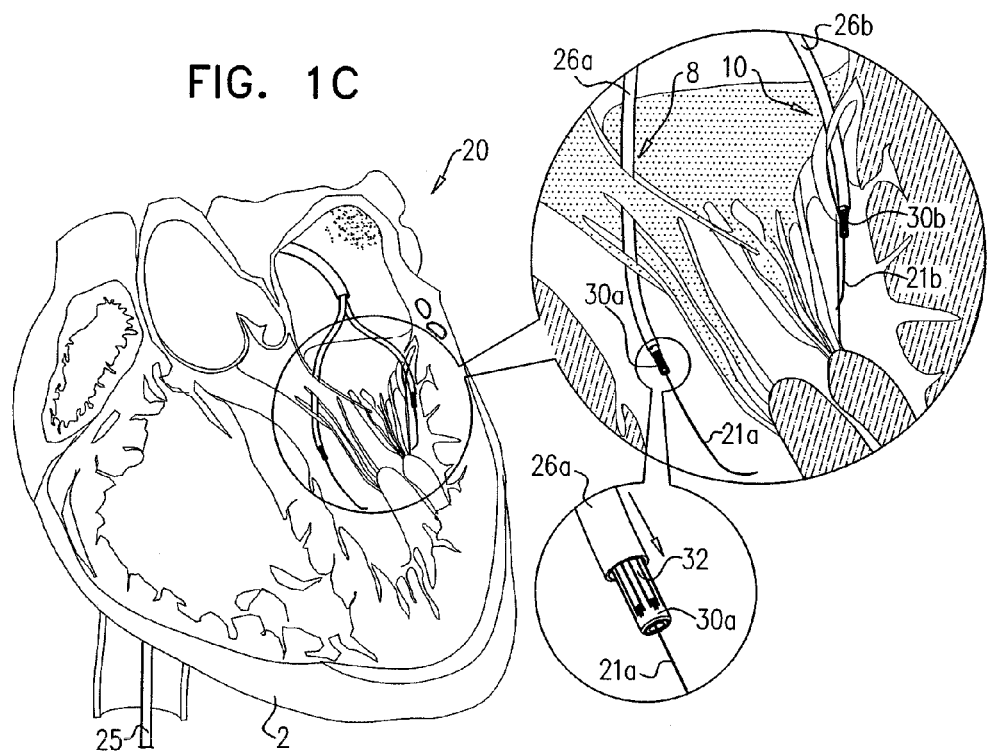
FIGS. 1C-D are schematic illustrations of the advancement and deployment of commissural anchors via the guide members, in accordance with some applications of the present invention.

Reference is now made to FIGS. 1A-B, which are schematic illustrations of a system 20 for replacing an atrioventricular valve 5 of a patient comprising one or more guide members 21a and 21b which are advanced toward first and second commissures 8 and 10 of valve 5 of a heart 2 of the patient, in accordance with some applications of the present invention. For some applications, guide members 21a and 21b comprise distinct guide members. Alternatively (as shown in FIGS. 8A-F), only one guide member is looped through commissures 8 and 10 in a manner in which the guide member defines a looped portion between commissures 8 and 10 (i.e., a portion of the guide member that is disposed in a ventricle 6 of heart 2), and first and second free ends which are disposed and accessible at a site outside the body of the patient. For such applications, the guide member defines portions 21a and 21b.

For some applications, guide members 21a and 21b comprise guide wires having a diameter of 0.035 inches.

The transcatheter procedure typically begins with the advancing of a semi-rigid guide wire into a right atrium 4 of the patient. The semi-rigid guide wire provides a guide for the subsequent advancement of a sheath 25 therealong and into the right atrium. Once sheath 25 has entered the right atrium, the semi-rigid guide wire is retracted from the patient's body. Sheath 25 typically comprises a 13-20 F sheath, although the size may be selected as appropriate for a given patient. Sheath 25 is advanced through vasculature into the right atrium using a suitable point of origin typically determined for a given patient. For example:

sheath 25 may be introduced into the femoral vein of the patient, through an inferior vena cava, into the right atrium, and into the left atrium transseptally, typically through the fossa ovalis;

sheath 25 may be introduced into the basilic vein, through the subclavian vein to the superior vena cava, into the right atrium, and into the left atrium transseptally, typically through the fossa ovalis; or sheath 25 may be introduced into the external jugular vein, through the subclavian vein to the superior vena cava, into the right atrium, and into the left atrium transseptally, typically through the fossa ovalis.

In some applications of the present invention, sheath is advanced through the inferior vena cava of the patient and into the right atrium using a suitable point of origin typically determined for a given patient.

Sheath 25 is advanced distally until sheath 25 reaches the interatrial septum. For some applications, a resilient needle and a dilator (not shown) are advanced through the sheath and into the heart. In order to advance the sheath transseptally into the left atrium, the dilator is advanced to the septum, and the needle is pushed from within the dilator and is allowed to puncture the septum to create an opening that facilitates passage of the dilator and subsequently the sheath therethrough and into the left atrium. The dilator is passed through the hole in the septum created by the needle. Typically, the dilator is shaped to define a hollow shaft for passage along the needle, and the hollow shaft is shaped to define a tapered distal end. This tapered distal end is first advanced through the hole created by the needle. The hole is enlarged when the gradually increasing diameter of the distal end of the dilator is pushed through the hole in the septum.

The advancement of sheath 25 through the septum and into the left atrium is followed by the extraction of the dilator and the needle from within sheath 25.

FIGS. 1C-D and 2A-B show advancement of one or more tissue anchors 30a and 30b along guide members 21a and 21b, respectively. Anchors 30a and 30b comprise a flexible, biocompatible material (e.g., nitinol) and comprise one or more (e.g., a plurality of) radially-expandable prongs 32 (e.g., barbs). Each anchor 30a and 30b is reversibly coupled to a respective delivery lumen 27a and 27b. Each delivery lumen 27 slides around a respective guide member 21. A respective surrounding sheath 26a and 26b surrounds each delivery lumen 27a and 27b and around anchors 30a and 30b at least in part in order to compress and prevent expansion of prongs 32 of tissue anchors 30a and 30b.

Figure 1D:
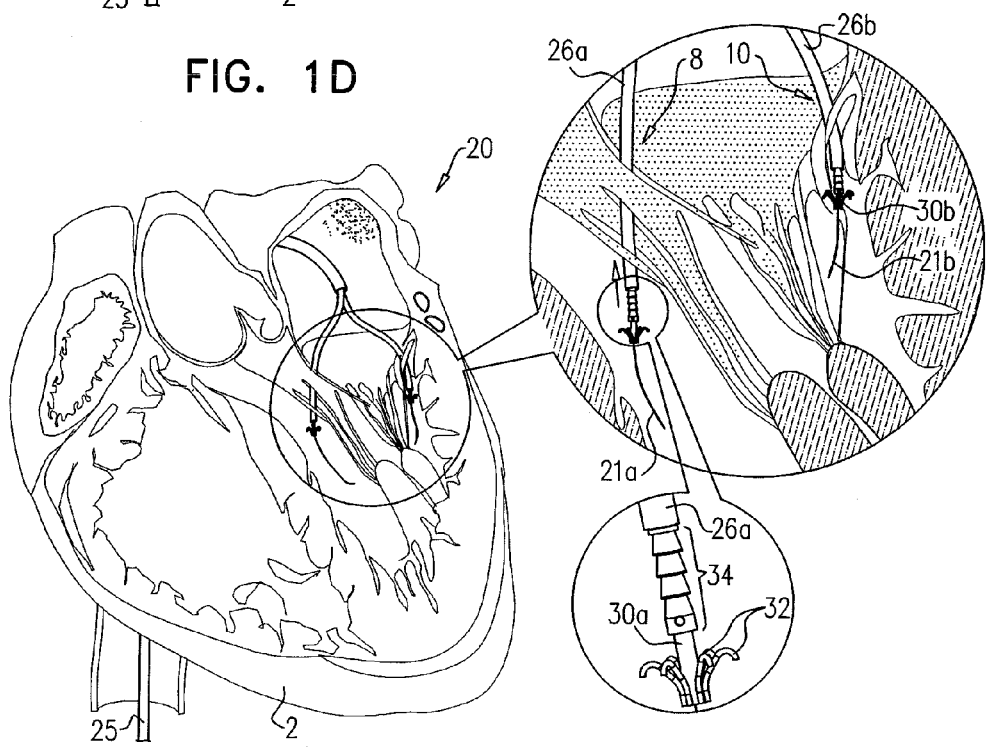

As shown in FIG. 1D, the distal ends of lumens 27a and 27b are reversibly coupled to ribbed crimping structures 34. As described hereinbelow, anchors 30a and 30b are anchored to ventricular surfaces of commissures 8 and 10. Following the anchoring, ribbed crimping structures 34 extend from anchors 30a and 30b through commissures 8 and 10, respectively, and toward the atrial surfaces of commissures 8 and 10. Ribbed crimping structures 34 are configured to facilitate anchoring of a valve support (described hereinbelow) to the atrial surfaces of commissures 8 and 10.

Anchors 30a and 30b, ribbed crimping structures 34, and the distal ends of surrounding sheaths 26a and 26b are advanced into ventricle 6. Subsequently, anchors 30a and 30b are pushed distally from within sheaths 26a and 26b, (or sheaths 26a and 26b are pulled proximally with respect to anchors 30a and 30b) to expose anchors 30a and 30b. As anchors 30a and 30b are exposed from within sheaths 26a and 26b, prongs 32 are free to expand, as shown in FIG. 1D. Prongs 32 expand such that anchors 30a and 30b assume a flower shape. Prongs 32, collectively in their expanded state, create a larger surface area to engage tissue than in their compressed states. Following the exposing of anchors 30a and 30b, sheaths 26a and 26b are extracted.

Figure 2A:
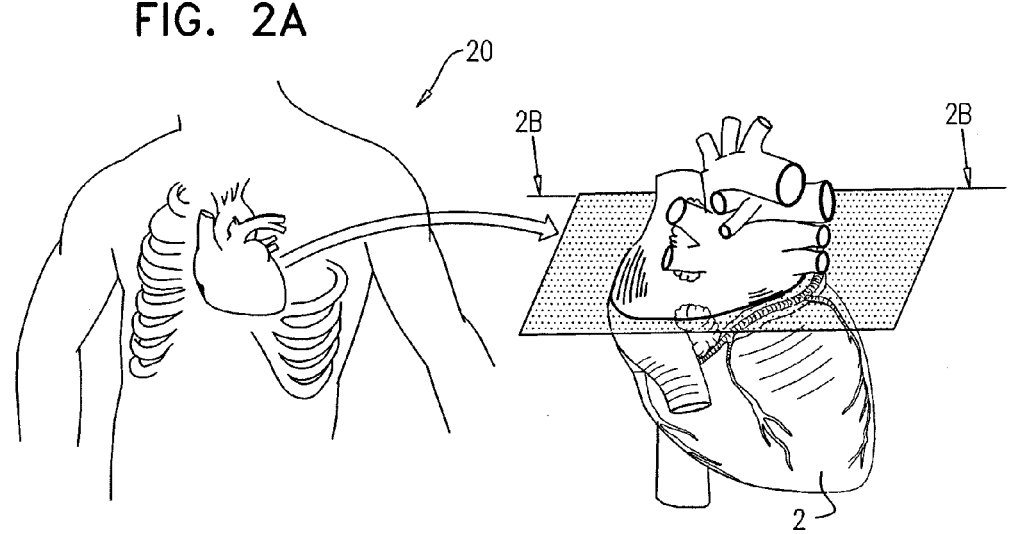
FIGS. 2A-D are schematic illustrations of the advancement of a prosthetic valve support toward a native atrioventricular valve of a patient, in accordance with some applications of the present invention.
Figure 2B:
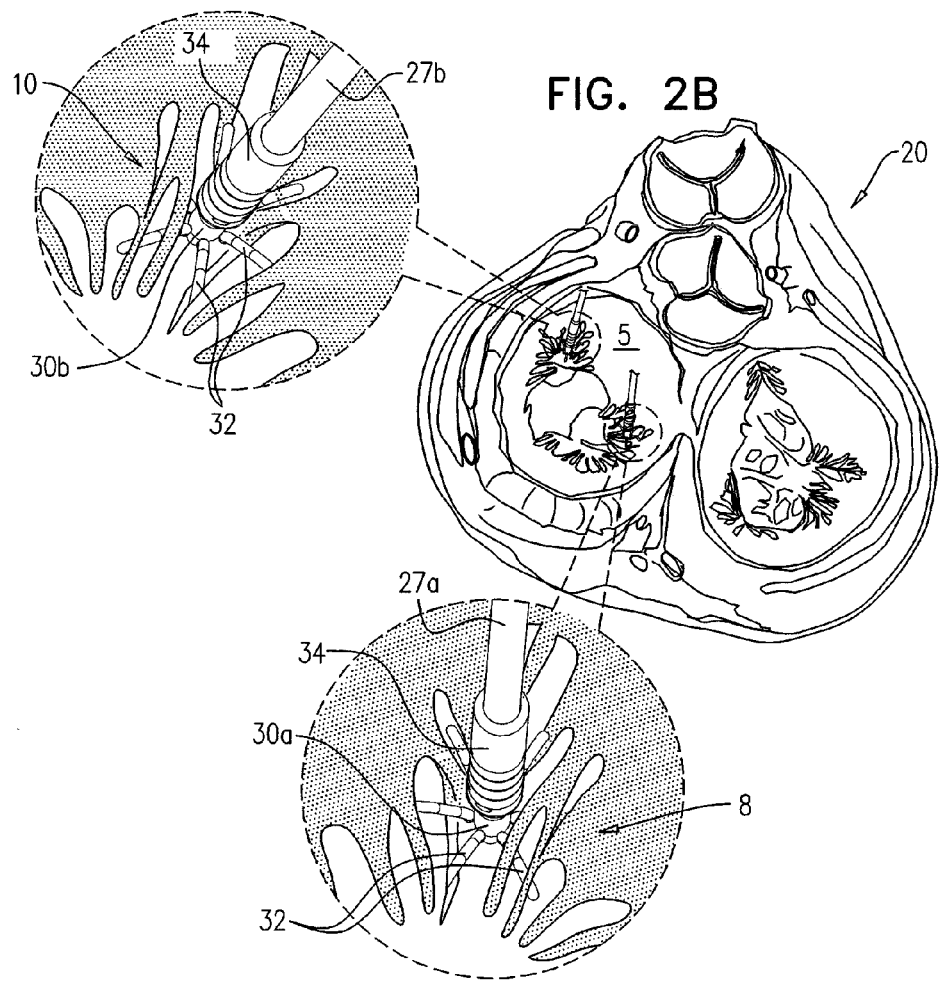
Figure 2C:
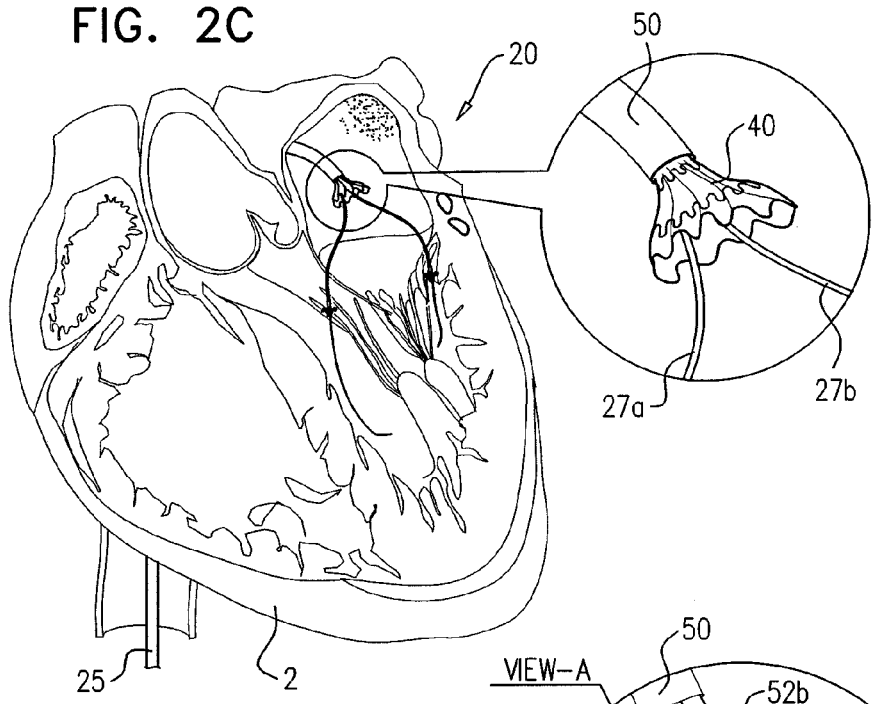

As shown in FIG. 2B, lumens 27a and 27b are pulled proximally so that prongs 32 of anchors 30a and 30b engage respective ventricular surface of commissures 8 and 10. Prongs 32 create a large surface area which restricts proximal motion of anchors 30a and 30b from commissures 8 and 10, respectively.

For some applications, following the anchoring of anchors 30a and 30b to commissures 8 and 10, respectively, guide members 21a and 21b are removed from the body of the patient.

Figure 2D:
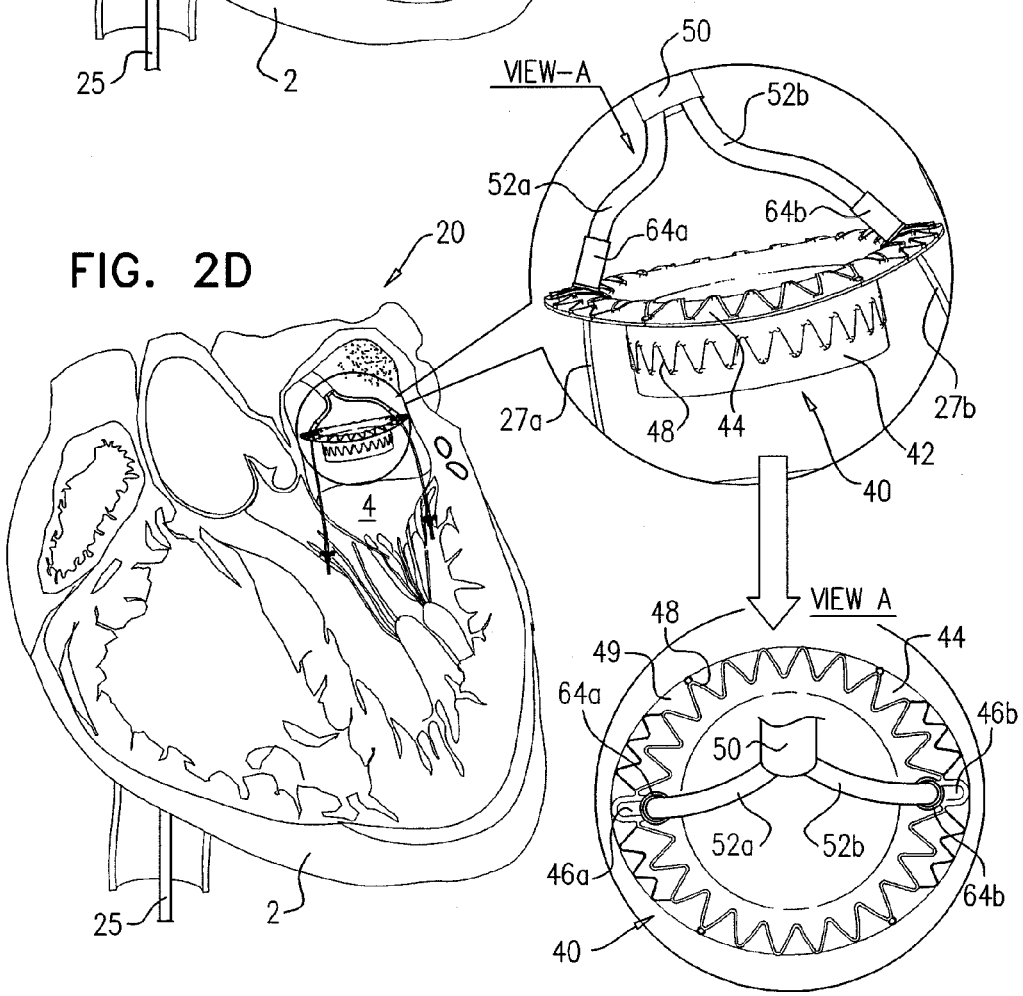

Reference is now made to FIGS. 2C-F, which are schematic illustrations of the advancement of a prosthetic valve support 40 along lumens 27a and 27b, in accordance with some applications of the present invention. In such a manner, lumens 27a and 27b function as valve support guide members. Support 40 comprises a collapsible skirt having a proximal annular element 44 and a distal cylindrical element 42. Support 40 is configured to assume a collapsed state (e.g., surrounded by a sheath or overtube 50 shown in FIG. 2C) for minimally-invasive delivery to the diseased native valve, such as by percutaneous or transluminal delivery using one or more catheters. FIG. 2O and the other figures show support 40 in an expanded state after delivery in right atrium 4 and advancement toward the native valve. As shown in FIG. 2D, support 40 is shaped so as to define one or more (e.g., two, as shown in View A) holes 46a and 46b for slidable advancement of support 40 along lumens 27a and 27b, respectively. That is, prior to introduction of support 40 into the body of the patient, lumens 27a and 27b are threaded through holes 46a and 46b, respectively, and support 40 is slid along lumens 27a and 27b. Support 40 is slid by pushing elements 52a and 52b which surround delivery lumens 27a and 27b, respectively.

It is to be noted that support 40 is slid along lumens 27a and 27b by way of illustration and not limitation. That is, for some applications, following the anchoring of anchors 30a and 30b to commissures 8 and 10, respectively, guide members 21a and 21b are not removed from the body of the patient, but rather lumens 27a and 27b are removed (e.g., by being decoupled from crimping structures 34) leaving behind anchors 30a and 30b and guide members 21a and 21b. Guide members 21a and 21b may then be threaded through holes 46a and 46b, respectively, and support 40 is slid along guide members 21a and 21b. In such a manner, guide members 21a and 21b function as valve support guide members.

Figure 2E:
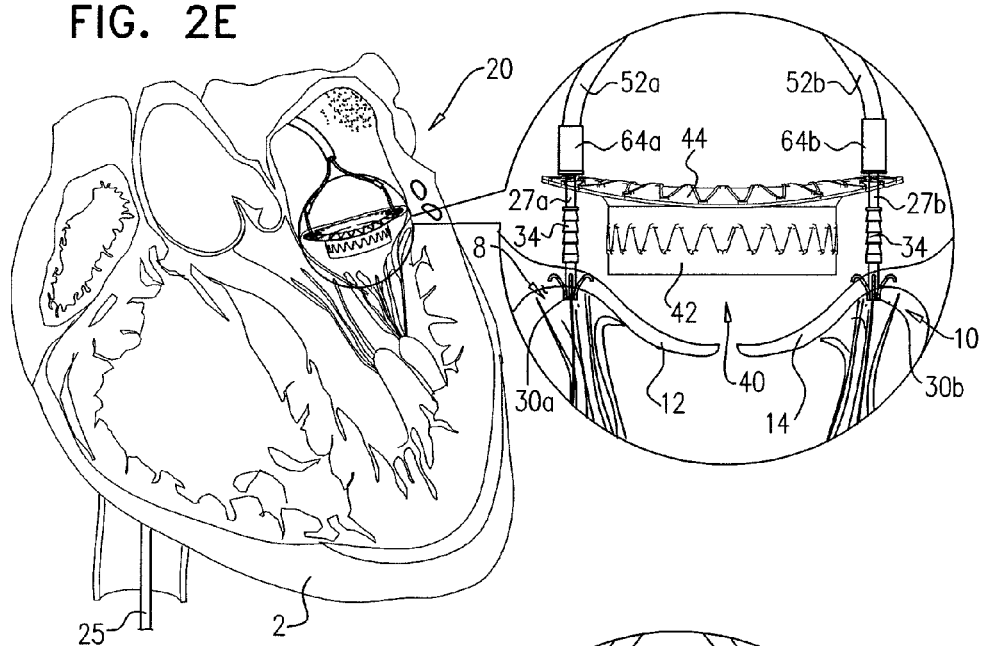
FIGS. 2E-F are schematic illustrations of locking of the prosthetic valve support at the native valve, in accordance with some applications of the present invention.

Support 40 comprises a collapsible flexible support frame 48, which is at least partially covered by a covering 49. Support 40 is configured to be placed at native valve 5, such that cylindrical element 42 passes through the orifice of the native valve and extends towards, and, typically partially into, ventricle 6 (as shown in FIG. 2E). Cylindrical element 42 typically pushes aside and presses against native leaflets of native valve 5 at least in part, which are left in place during and after implantation of the prosthetic valve. Annular element 44 is configured to be placed around a native annulus 11 of the native valve, and to extend at least partially into an atrium 4 such that annular element 44 rests against the native annulus. Annular element 44 is typically too large to pass through the annulus, and may, for example, have an outer diameter of between 30 and 60 mm.

For some applications, collapsible support frame 48 comprises a stent, which comprises a plurality of struts. The struts may comprise, for example, a metal such as nitinol or stainless steel. For some applications, frame comprises a flexible metal, e.g., nitinol, which facilitates compression of support 40 within a delivery sheath or overtube 50. For some applications, covering 49 comprises a fabric, such as a woven fabric, e.g., Dacron. Covering 49 is typically configured to cover at least a portion of cylindrical element 42, and at least a portion of annular element 44. The covering may comprise a single piece, or a plurality of pieces sewn together.

As shown in FIG. 2D, pushing elements 52a and 52b are each coupled to locking crimping elements 64a and 64b, respectively. Locking crimping elements 64a and 64b are disposed adjacently, proximally to holes 46a and 46b respectively of valve support 40. These techniques enable the surgeon to readily bring crimping elements 64a and 64b to the appropriate sites along annular element 44, without the need for excessive imaging, such as fluoroscopy.

FIG. 2E shows valve support 40 prior to implantation at annulus 11. As shown, ribbed crimping structures 34 project away from anchors 30a and 30b, through commissures 8 and 10, and toward atrium 4. Valve support 40 is advanced along lumens 27a and 27b toward structures 34 by being pushed by pushing elements 52a and 52b and locking crimping elements 64a and 64b.

Figure 2F:
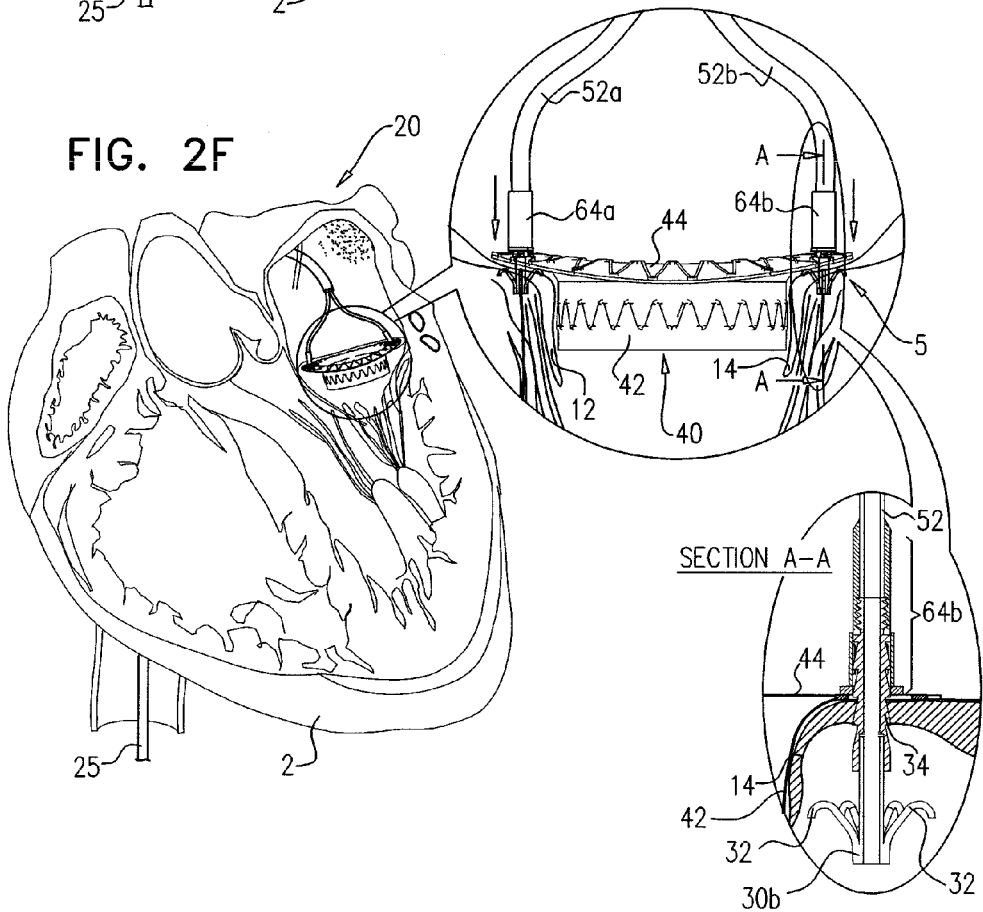

In FIG. 2F, valve support 40 is further pushed by pushing elements 52a and 52b and locking crimping elements 64a and 64b such holes 46a and 46b of support 40 advance around ribbed crimping structures 34. As holes 46a and 46b are advanced around ribbed crimping structures 34, locking crimping elements 64a and 64b advance over and surround ribbed crimping elements 34 to lock in place valve support 40 from an atrial surface of valve 5.

Responsively to the placement of valve support 40 at native valve 5, cylindrical element 42 is positioned partially within ventricle 6 and native leaflets 12 and 14 of native valve 5 are pushed aside.

As shown in section A-A, ribbed crimping structures 34 are shaped so as to define a plurality of male couplings. Locking crimping elements 64a and 64b each comprise a cylindrical element having an inner lumen that is shaped so as to surround a respective ribbed crimping structure 34. Each inner lumen of locking crimping elements 64a and 64b is shaped so as to define female couplings to receive the male couplings of ribbed crimping structure 34. The female couplings of locking crimping element 64 are directioned such that they facilitate distal advancement of locking crimping element 64 while restricting proximal advancement of locking crimping element 64. When the female couplings of locking crimping element 64 receive the male couplings of ribbed crimping structure 34, valve support 40 is locked in place from an atrial surface of valve 5. It is to be noted that for some applications, ribbed crimping elements 34 comprise female couplings, and locking crimping elements 64 comprise male couplings.

Reference is now made to FIGS. 2G-K which are schematic illustrations of the coupling of a prosthetic atrioventricular valve 80 to valve support 40, in accordance with some applications of the present invention. Support 40 receives the prosthetic valve and functions as a docking station. Thus, the docking station is a coupling element that provides coupling between two other elements (in this case, between annulus 11 and the prosthetic valve.)

Figure 2G:
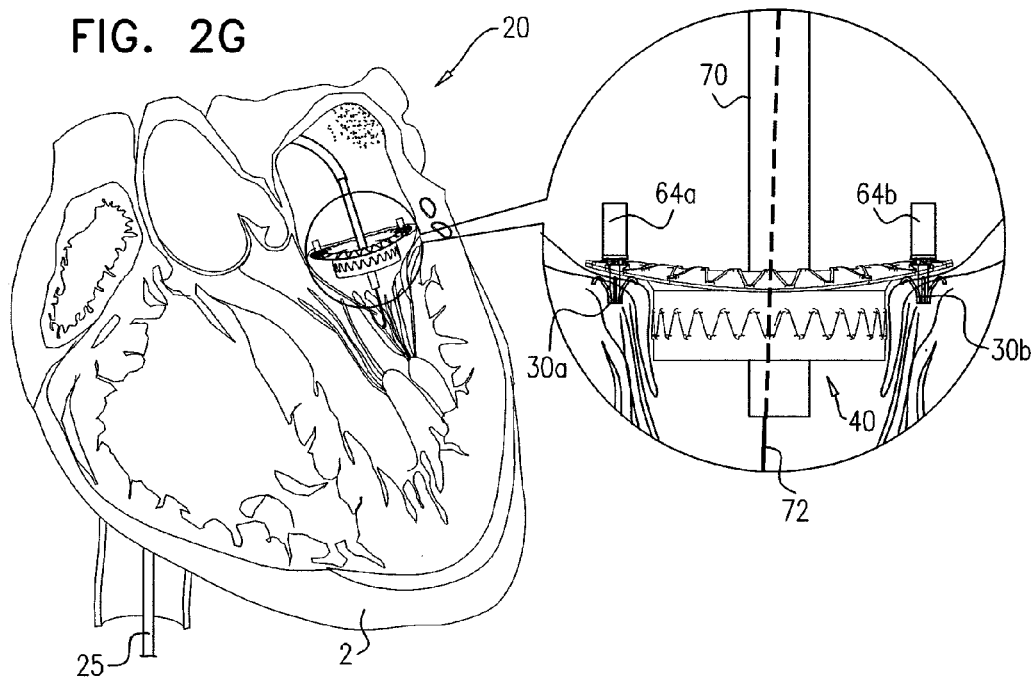

Following the placement of support 40 at annulus 11, pushing elements 52a and 52b and sheath or overtube 50 are removed from the body of the patient, leaving behind lumens 27a and 27b, as shown in FIG. 2G.

As shown in FIG. 2G, a guide wire 72 is advanced toward ventricle 6 and facilitates the advancement of an overtube 70 through sheath 25 and the positioning of a distal end of overtube 70 within ventricle 6. Overtube 70 facilitates the advancement of prosthetic valve 80 in a compressed state, toward valve support 40.

Figure 2H:
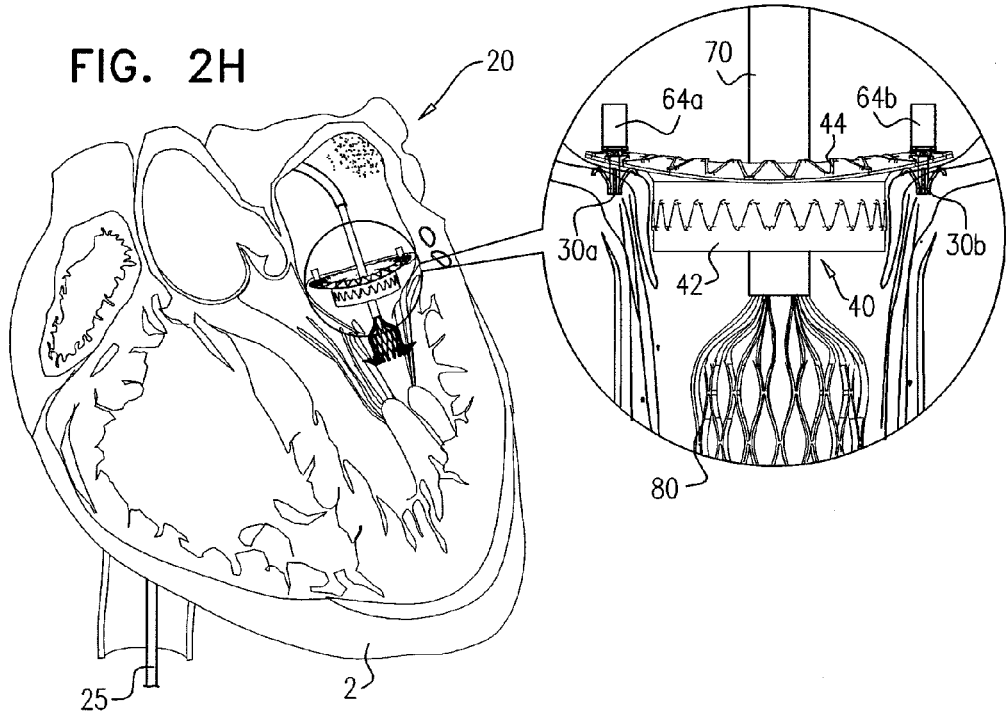

FIG. 2H shows partial deployment of valve 80 within ventricle 6 of heart 2. Valve 80 is shown comprising a flexible wire frame comprising a plurality of stent struts by way of illustration and not limitation. The wireframe of valve 80 comprises a flexible metal, e.g., nitinol or stainless steel. It is to be noted that the wireframe of valve 80 is covered by a covering (not shown for clarity of illustration) comprising a braided mesh or in a fabric such as a woven fabric, e.g., Dacron. The covering is typically configured to cover at least a portion of the frame. The covering may comprise a single piece, or a plurality of pieces sewn together.

Following the partial deployment of valve 80 in ventricle 6, overtube 70 is pulled proximally to pull valve 80 proximally such that cylindrical element 42 of valve support 40 surrounds a proximal portion of prosthetic valve 80. Valve 80 has a tendency to expand such that valve 80 is held in place with respect to valve support 40 responsively to radial forces acted upon valve support 40 by prosthetic valve 80.

Valve 80 comprises a plurality of distal protrusions (e.g., snares). When valve 80 is pulled proximally, as described hereinabove, protrusions 84 ensnare and engage the native leaflets of the atrioventricular valve. By the ensnaring of the native leaflets, protrusions 84 sandwich the native valve between protrusions 84 and prosthetic valve support 40. Such ensnaring helps further anchor prosthetic valve 80 to the native atrioventricular valve. The scope of the present invention includes using any sort of protrusions (e.g., hooks) that protrude from the distal end of the main frame of prosthetic valve 80 and that are configured such that the native valve is sandwiched between the protrusions and valve support 40. Typically, the protrusions cause sandwiching of the native valve leaflets, such that the leaflets do not interfere with the left ventricular outflow tract (LVOT).

For some applications, during the procedure, the prosthetic valve is pulled back proximally with respect to valve support, as described hereinabove. The prosthetic valve is pulled back to a position with respect to valve support that is such that protrusions 84 prevent the native leaflets from interfering with the LVOT, by sandwiching the native leaflets between the protrusions and the valve support. The prosthetic valve is then deployed at this position.

For some applications, protrusions are disposed on the valve on the sides of the valve that are adjacent to the anterior and posterior leaflets of the native valve, and the valve does not includes protrusions on the portions of the valve that are adjacent to the commissures of the native valve, as described with reference to FIGS. 11A-D. For some applications, the protrusions are disposed in a sinusoidal configuration in order to conform with the saddle shape of the native valve, as described hereinbelow with reference to FIGS. 12A-C.

Additionally, as shown in FIG. 2J, valve 80 comprises one or more (e.g., a plurality, as shown) coupling elements 81 at the proximal end of valve 80. Overtube 70, which facilitates the advancement of prosthetic valve 80, is reversibly coupled to valve 80, via coupling elements 81.

Prosthetic valve 80 is configured for implantation in and/or at least partial replacement of a native atrioventricular valve 5 of the patient, such as a native mitral valve or a native tricuspid valve. Prosthetic valve 80 is configured to assume a collapsed state for minimally-invasive delivery to the diseased native valve, such as by percutaneous or transluminal delivery using one or more catheters. FIG. 2J shows prosthetic valve 80 in an expanded state after delivery to the native valve.

Figure 2K:
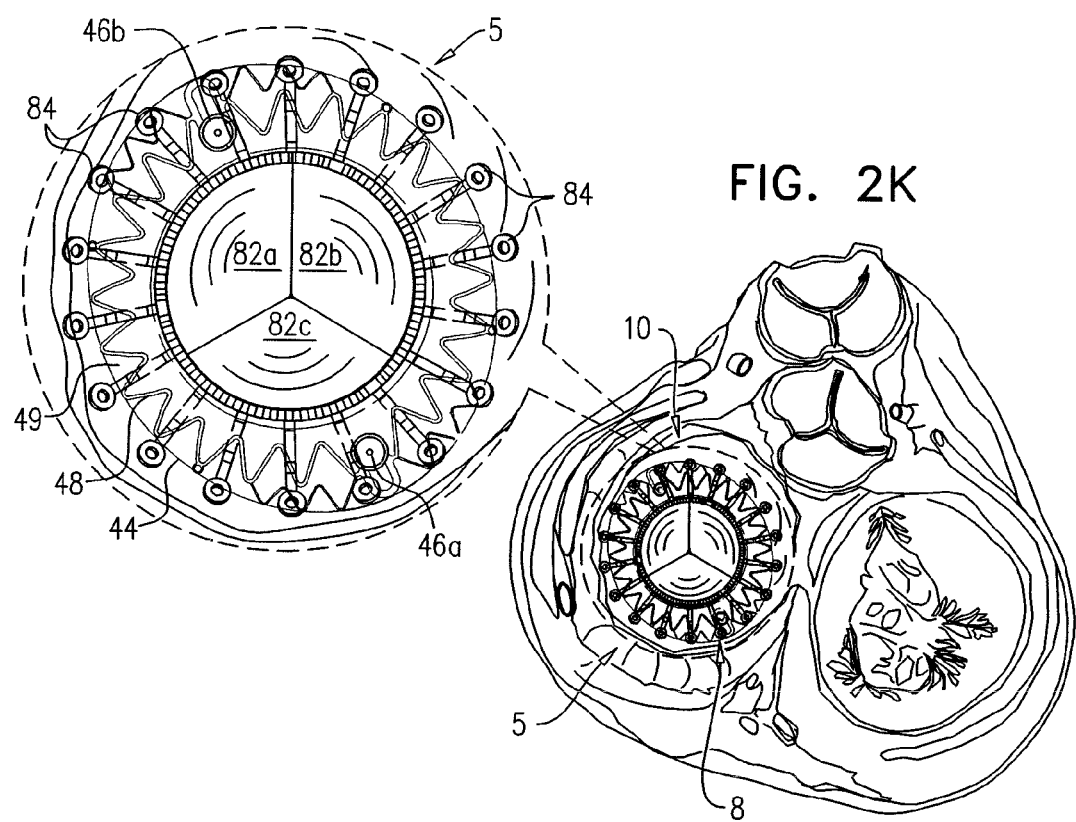

Reference is now made to FIG. 2K which shows a bird's-eye view of valve 80. Prosthetic valve 80 further comprises a plurality of valve leaflets 82, which may be artificial or tissue-based. The leaflets are typically coupled to an inner surface of the valve prosthesis. Leaflets 82 are coupled, e.g., sewn, to the frame and/or to the covering. For applications in which the prosthetic valve is configured to be implanted at the native mitral valve, the prosthetic valve typically comprises three leaflets 82a, 82b, and 82c, as shown in FIG. 2K.

Figure 3A:
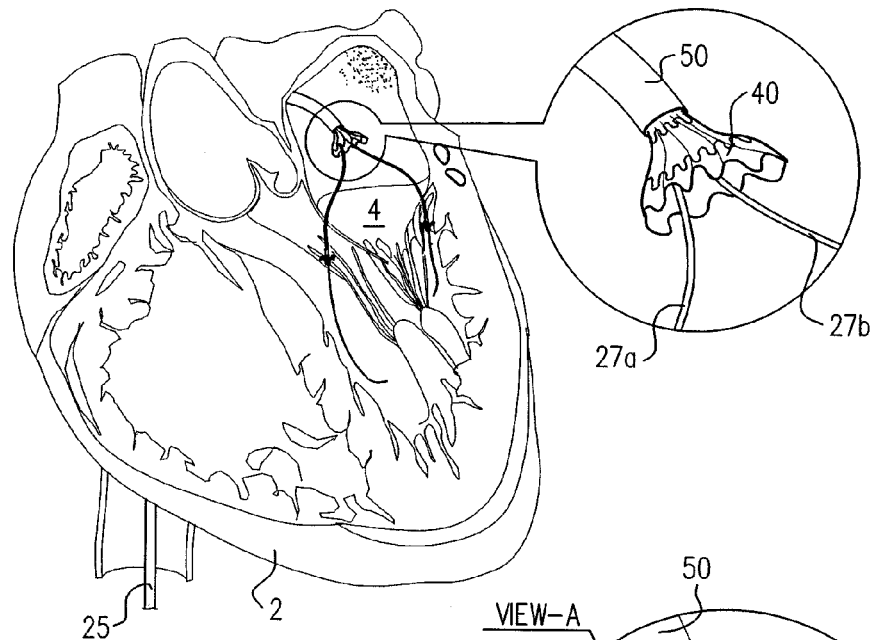
FIGS. 3A-B are schematic illustrations of the advancement of a prosthetic valve support toward a native atrioventricular valve of a patient, the valve support including a sealing balloon, in accordance with some applications of the present invention.
Figure 3B:
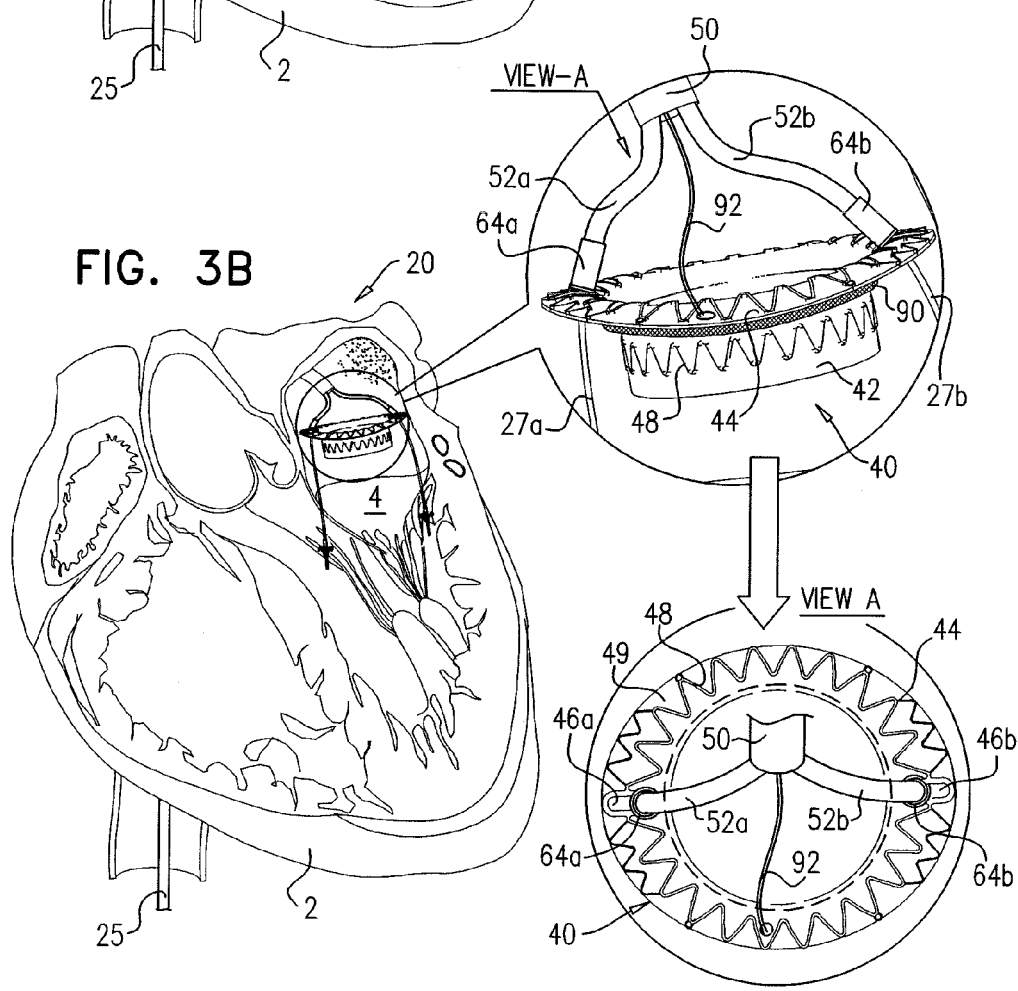

Reference is now made to FIGS. 3A-D, which are schematic illustrations of the advancement of prosthetic valve support 40 toward native atrioventricular valve 5 of a patient, the valve support including a sealing balloon 90, in accordance with some applications of the present invention. The steps shown in FIGS. 3A-C are generally similar to those shown in FIGS. 2C-F. For some applications, sealing balloon 40 is disposed on the valve-facing, lower side of annular element 44 of the prosthetic valve support. FIG. 3D shows valve support 40, the valve support having been implanted at annulus 11. Typically, at this stage, balloon 40 is inflated, as shown in the transition from FIG. 3C to FIG. 3D. The balloon is inflated via an inflation lumen 92, shown in FIG. 3C, for example. For some applications, the balloon seals the interface between the prosthetic valve support and native annulus 11, thereby reducing retrograde blood flow from ventricle 6 into atrium 4, relative to retrograde blood flow in the absence of a sealing balloon. For some applications, the balloon is inflated prior to the placement of the prosthetic support at annulus 11.

Figure 4A:
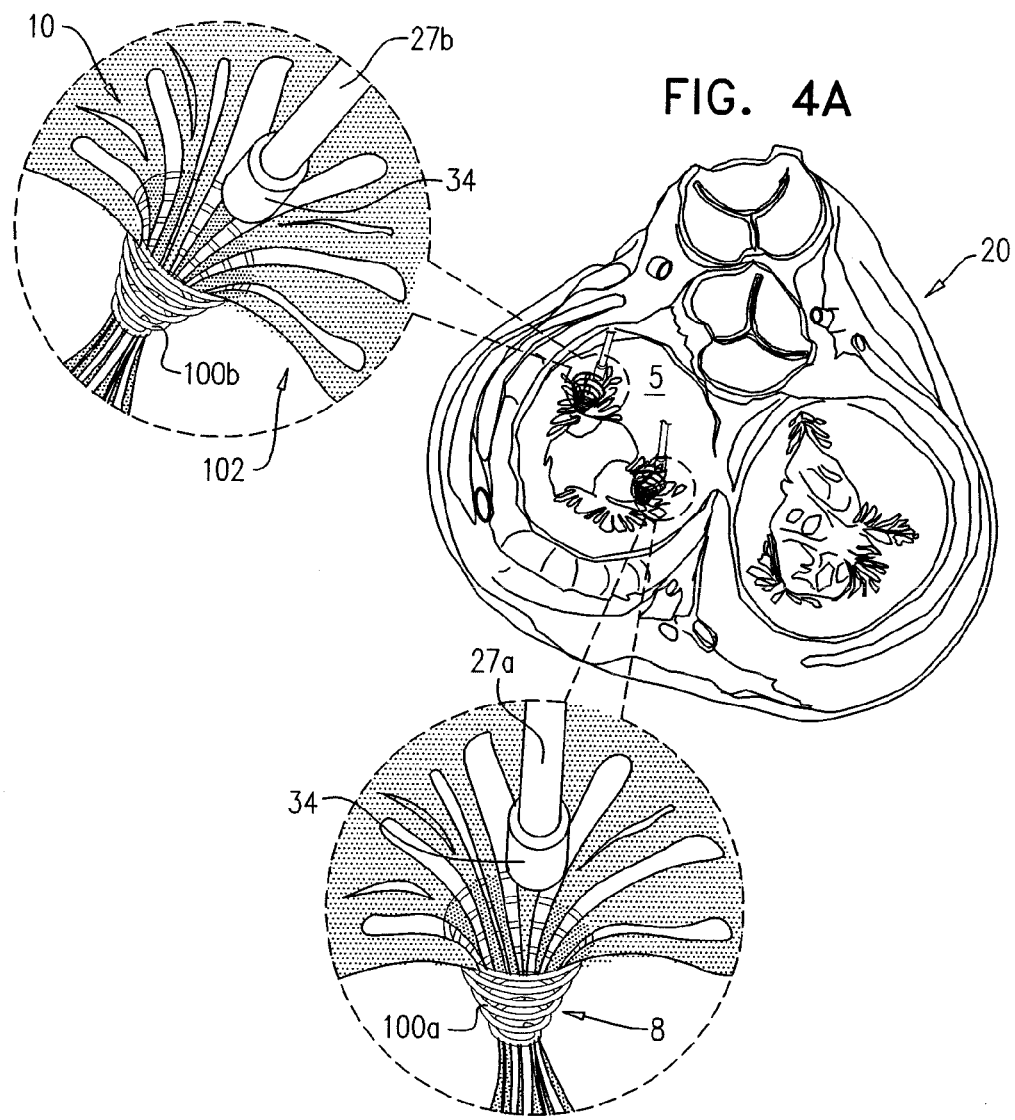
FIGS. 4A-C are schematic illustrations of a valve support being used with commissural helices that facilitate anchoring and/or sealing of the valve support, in accordance with some applications of the present invention.
Figure 4B:
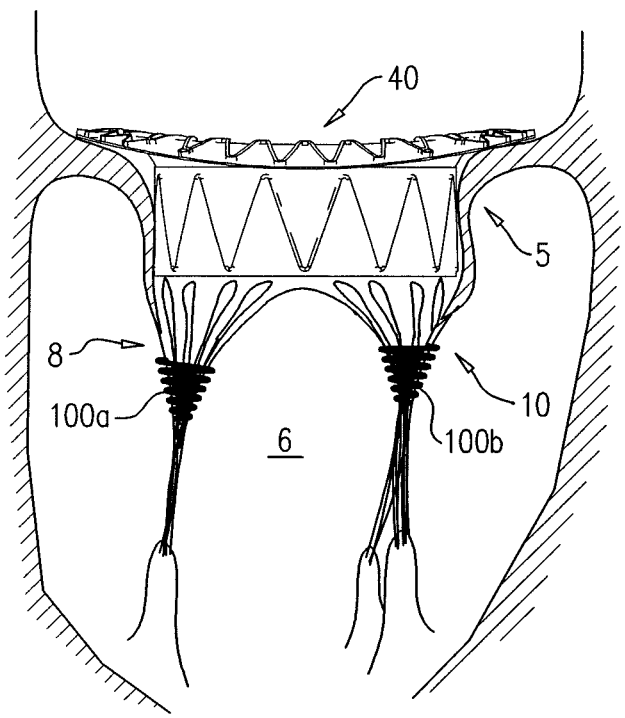
Figure 4C:
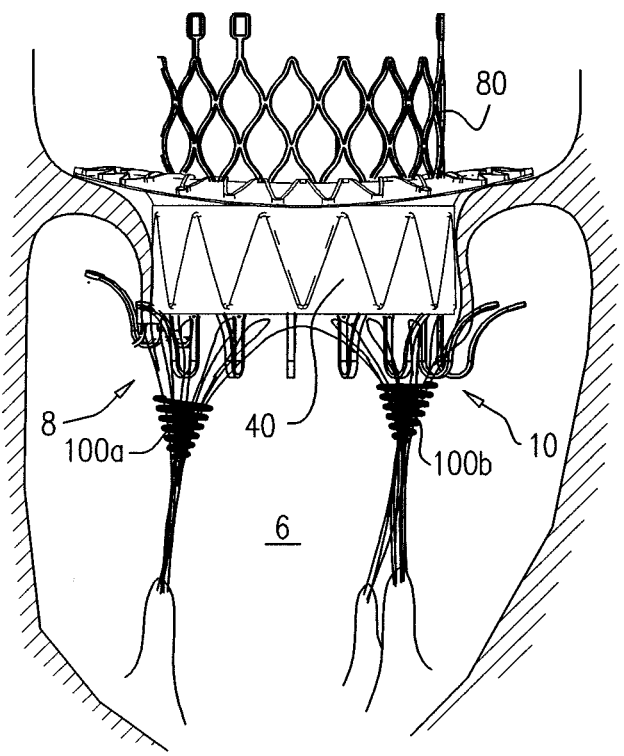

Reference is now made to FIGS. 4A-C, which are schematic illustrations of prosthetic valve support 40 being used with commissural helices 100a and 100b that facilitate anchoring and/or sealing of the valve support, in accordance with some applications of the present invention. For some applications, commissural helices are used as an alternative or in addition to anchors 30a and 30b and/or other anchoring elements described herein, in order to facilitate the anchoring of valve support 40.

Commissural helices 100a and 100b are typically placed at commissures 8 and 10 in a generally similar technique to that described with reference to anchors 30a and 30b. Typically, each helix 30a and 30b is reversibly coupled to a respective delivery lumen 27a and 27b. As described above, each delivery lumen 27 slides around a respective guide member 21, and a respective surrounding sheath 26a and 26b surrounds each delivery lumen 27a and 27b.

Commissural helices 100a and 100b (optionally, ribbed crimping structures 34), and the distal ends of surrounding sheaths 26a and 26b are advanced into ventricle 6. The helices are pushed out of the distal ends of surrounding sheaths 26a and 26b. Subsequently, the helices are rotated proximally such that the helices wrap around at least some chordae tendineae 102 of the patient. Following the advancement of the helices out of sheaths 26a and 26b, the sheaths are extracted. For some applications the helices are conical helices (as shown), and the wider end of the conical helix is disposed at the proximal end of the helix.

Subsequent to the placement of commissural helices 100a and 100b around the chordae tendineae, prosthetic valve support 40 is placed at annulus 11, in accordance with the techniques described hereinabove, and as shown in FIG. 4B. Subsequently, prosthetic valve 80 is coupled to the prosthetic valve support, in accordance with the techniques described hereinabove, and as shown in FIG. 4C.

Typically, commissural helices 100a and 100b facilitate sealing of native commissures 8 and 10, thereby reducing retrograde blood flow via the commissures, relative to retrograde blood flow in the absence of the helices. Further typically, the sealing of the native commissures facilitates anchoring of the prosthetic valve support to native valve 5.

Figure 5A:
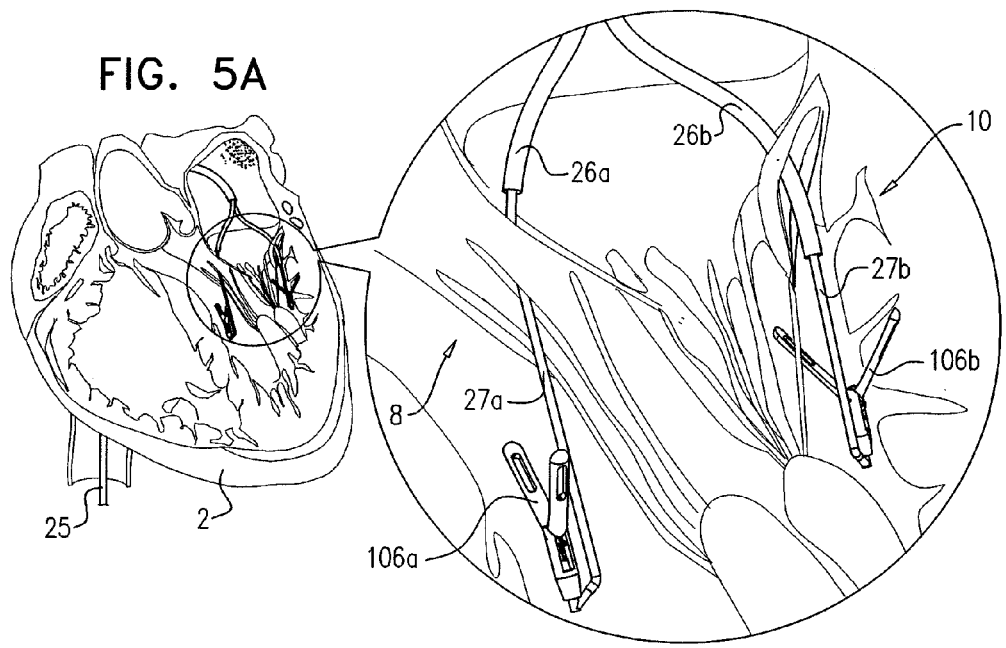
FIGS. 5A-D are schematic illustrations of grasping elements being used to anchor and/or provide sealing of a prosthetic valve, in accordance with some applications of the present invention.

Reference is now made to FIGS. 5A-D, which are schematic illustrations of grasping elements 106a and 106b being used to anchor prosthetic valve 80, in accordance with some applications of the present invention. For some applications, guide members 21a and 21b are advanced toward first and second commissures 8 and 10 of valve 5 of the patient, as described hereinabove. Grasping elements 106a and 106b are reversibly coupled to distal ends of delivery lumen 27a and 27b, the delivery lumens being advanced over respective guide members, as described hereinabove. For some applications, the guiding members and the grasping elements are advanced toward the patient's commissures via surrounding sheaths 26a and 26b, the surrounding sheaths being generally as described hereinabove. The grasping elements are typically placed distally to the commissures in a proximally-facing configuration, as shown in FIG. 5A. For example, as shown, the grasping elements may be configured to be proximally facing due to the coupling of the grasping elements to the guide members.

Figure 5B:
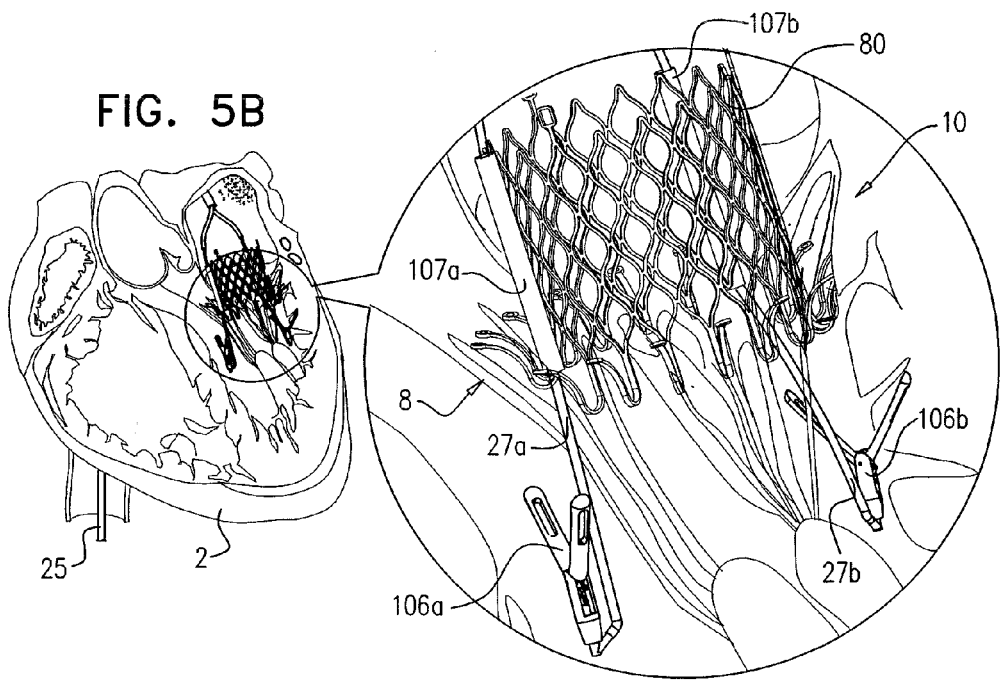
Figure 5C:
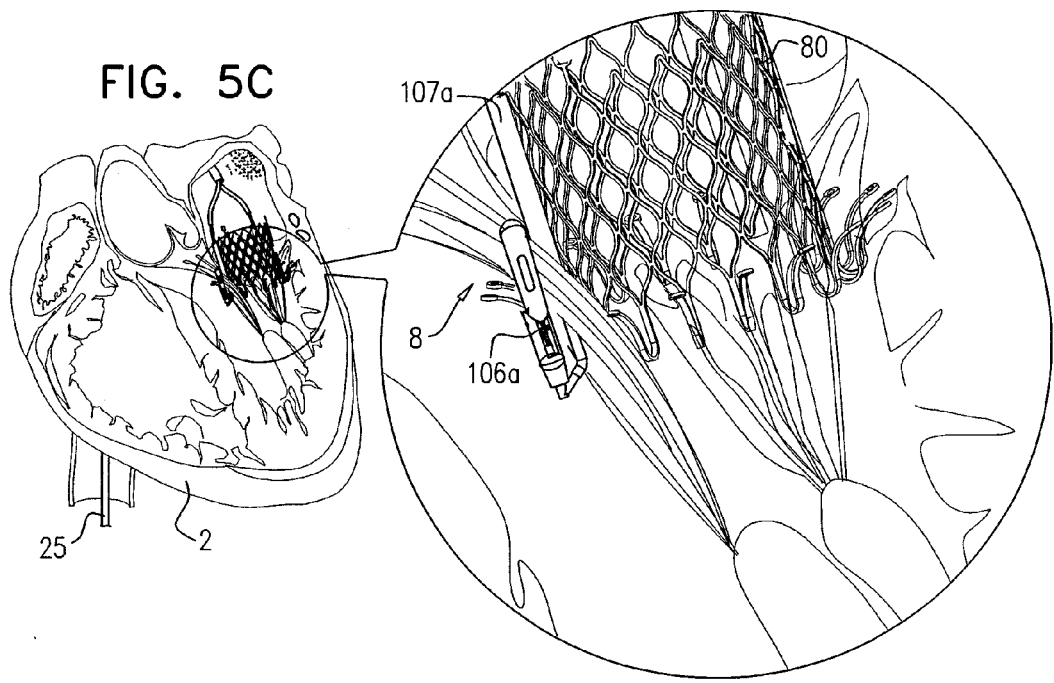
Figure 5D:
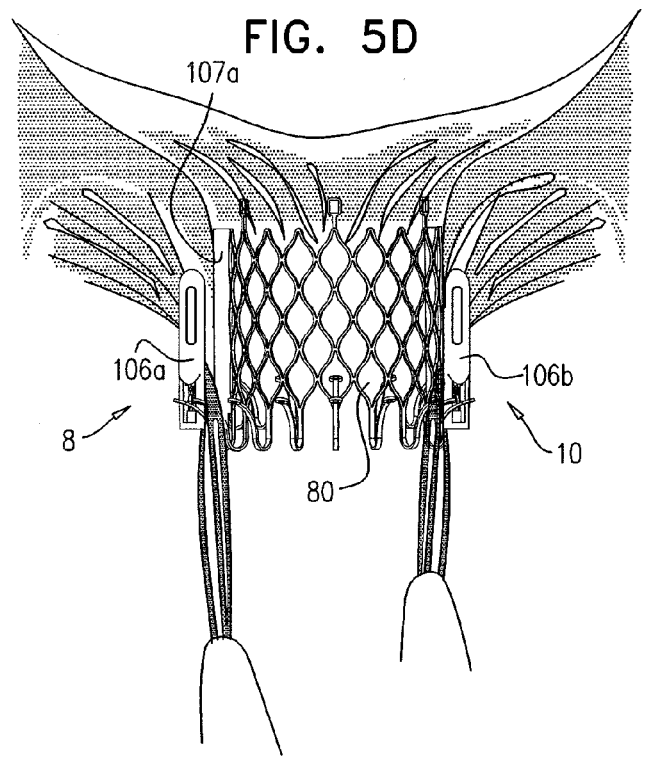

Subsequent to the placement of grasping elements 106a and 106b distally to native commissures 8 and 10, prosthetic valve 80 is advanced toward native valve 5, as shown in FIG. 5B. For example, the prosthetic valve may be advanced over delivery lumens 27a and 27b, as shown. The prosthetic valve is placed at the native valve and, subsequently, the grasping elements are retracted proximally toward commissures 8 and 10, as shown in the transition from FIG. 5B to FIG. 5C. For some applications, the grasping elements are coupled to valve 80 via coupling tubes 107a and 107b, the coupling tubes being coupled to the sides of the valve, as shown. The grasping elements are closed such that the native commissures are grasped and sealed by the grasping elements, as shown in FIG. 5D. Typically, the grasping elements define two surfaces that are hingedly coupled to each other. For example, the grasping elements may include forceps, as shown. The grasping elements are closed by closing the surfaces about the hinge, with respect to one another.

Typically, grasping elements 106a and 106b facilitate sealing of native commissures 8 and 10, thereby reducing retrograde blood flow via the commissures, relative to retrograde blood flow in the absence of the grasping elements. Further typically, the sealing of the native commissures facilitates anchoring of the prosthetic valve to native valve 5.

Although not shown, for some applications, prosthetic valve support 40 is used in addition to grasping elements 106a and 106b, in order to anchor prosthetic valve 80 to native valve 5. For some applications, the grasping elements are used to anchor and/or provide sealing for prosthetic valve support 40 (instead of, or in addition to, being used to anchor prosthetic valve 80, as shown). For such applications, generally similar techniques are used to those described with respect to the use of the grasping elements for anchoring the prosthetic valve, mutatis mutandis.

Figure 6A:
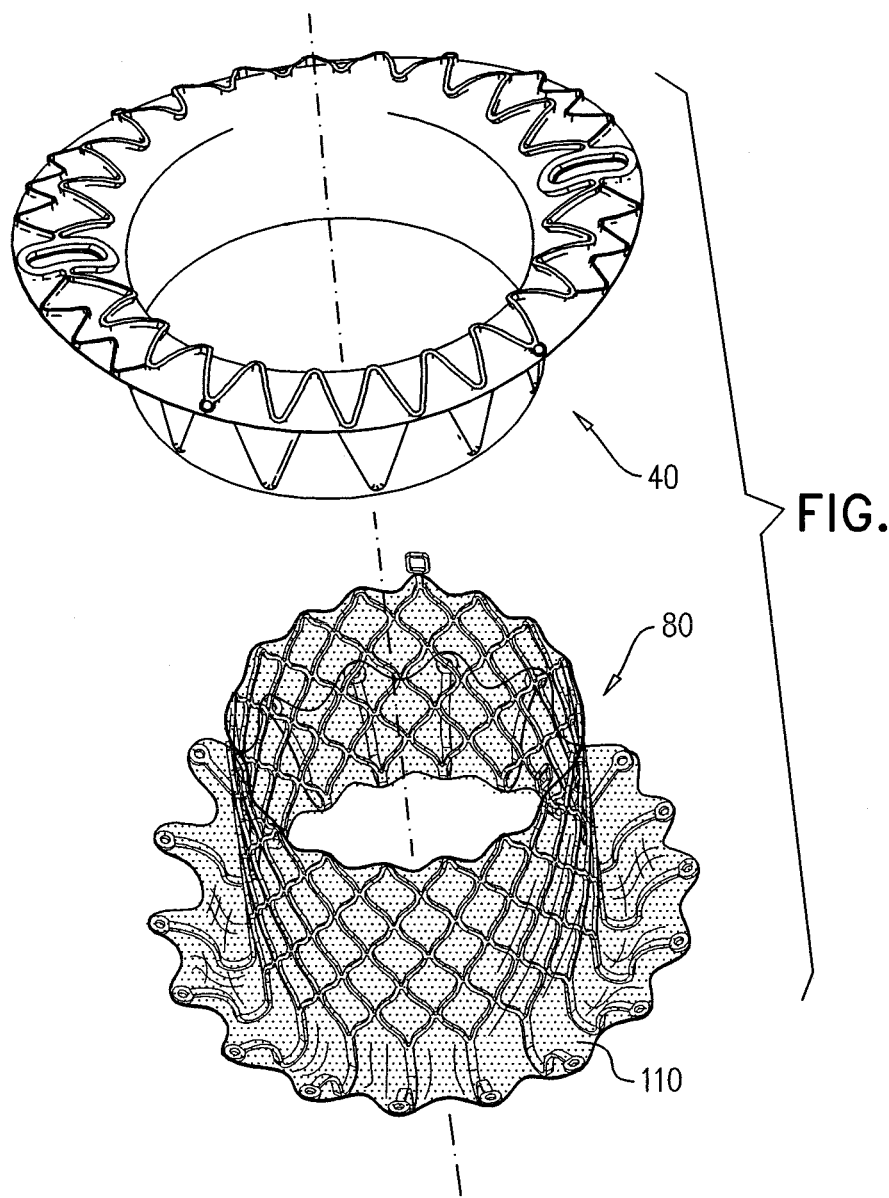
FIGS. 6A-B are schematic illustrations of a prosthetic valve that includes a sealing material, in accordance with some applications of the present invention.
Figure 6B:
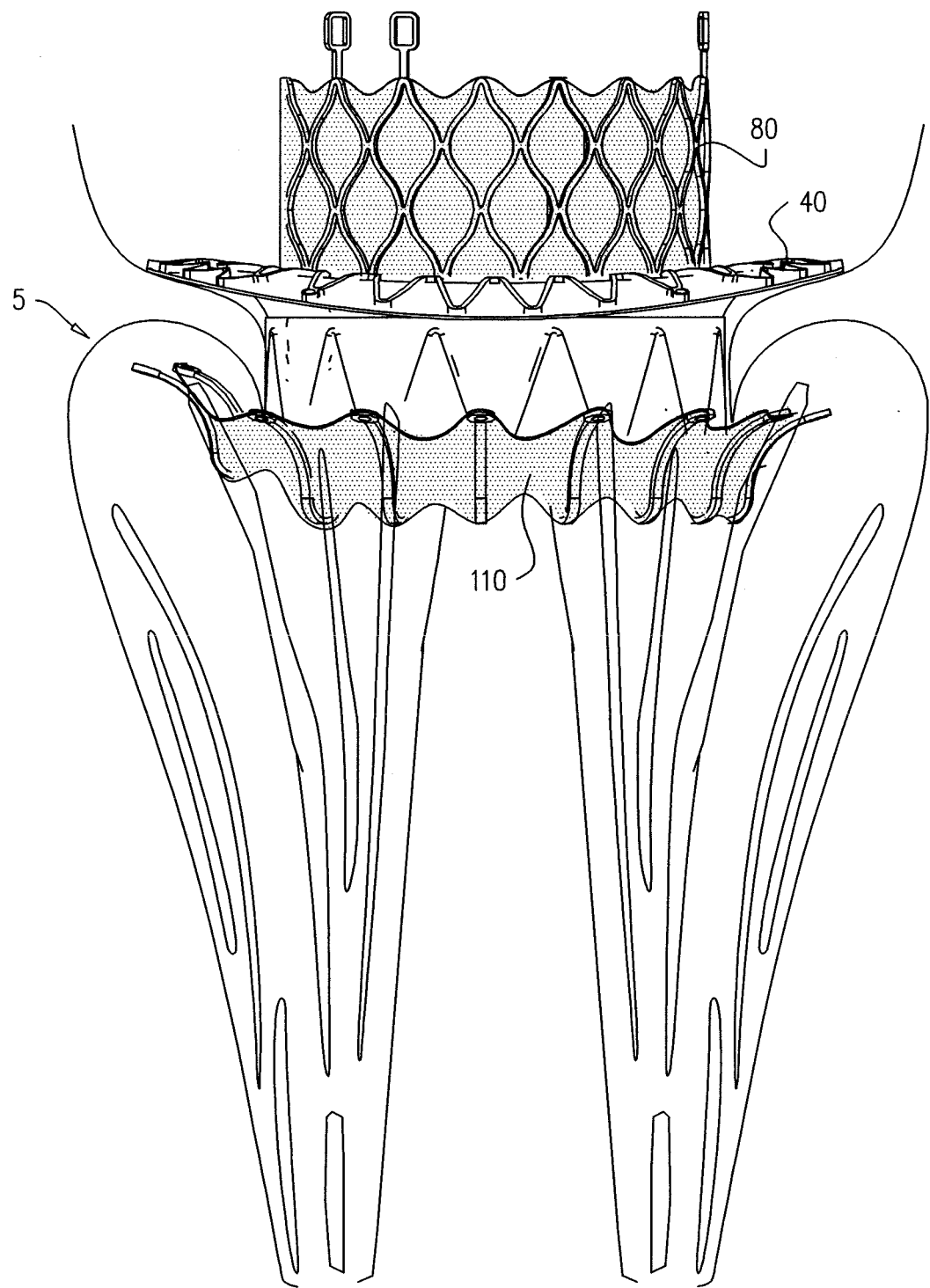

Reference is now made to FIGS. 6A-B, which are schematic illustrations of prosthetic valve 80, the prosthetic valve comprising a sealing material 110 on an outer surface of the valve, in accordance with some applications of the present invention. For some applications, prosthetic valve 80 is used in conjunction with prosthetic valve support 40, as described hereinabove. The techniques for implanting prosthetic valve 80 as shown in FIGS. 6A-B are generally similar to those described hereinabove. Typically, sealing material 110 seals the interface between the prosthetic valve and native valve 5. The sealing material reduces retrograde blood flow from ventricle 6 into atrium 4, relative to retrograde blood flow in the absence of the sealing material. Typically, the sealing material is composed of latex, dacron, and/or any other suitable biocompatible material. The sealing material is typically placed around at least a portion of the wire frame of the prosthetic valve so as to form a webbing between struts of the wire frame.

Reference is now made to FIGS. 7A-F, which are schematic illustrations of a guide wire delivery system, in accordance with some applications of the present invention. As described hereinabove (e.g., with reference to FIGS. 2C-F), for some applications, guide members 21a and 21b, function as valve support guide members, by support 40 being slid along guide members 21a and 21b. For some applications, only one guide member 21 is looped through commissures 8 and 10 in a manner in which the guide member defines a looped portion between commissures 8 and 10 (i.e., a portion of the guide member that is disposed in a ventricle 6 of heart 2), and first and second free ends, which are disposed and accessible at a site outside the body of the patient. For such applications, the guide member defines portions 21a and 21b.

Figure 7C:
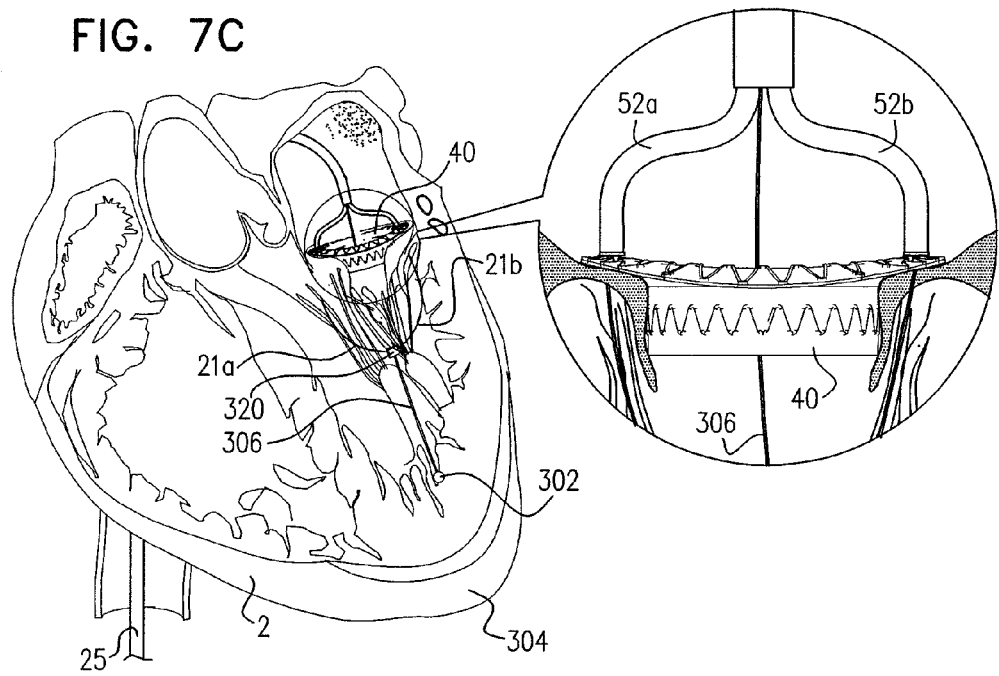

For some applications, an anchor 302 is advanced toward the vicinity of apex 304 of heart 2, via sheath 25, and is anchored to the vicinity of the apex, as shown in FIG. 7A. A guidewire 306 extends proximally from anchor. Guide member 21 passes through a guide member tube 320, the guide member tube being coupled to guidewire 306. Guide member 21 is pushed distally. Guide member tube 320 is unable to advance distally over guidewire 306, due to the coupling of the guide member tube to the guidewire. Therefore, the pushing of guide member 21 distally, causes portions 21a and 21b to spread apart from one another and to be pushed against commissures 8 and 10 of native valve 5. Portions 21a and 21b are then used to guide valve support 40 to the commissures, as shown in FIGS. 7B-F, using generally similar techniques to those described hereinabove, except for the differences described hereinbelow.

As shown in FIG. 7B, valve support 40 is slid over guide member portions 21a and 21b, by pushing elements 52a and 52b. Since the guide member portions are positioned at commissures 8 and 10, the guide member portions guide the distal ends of pushing elements 52a and 52b, such that the pushing elements push the valve support against the commissures, as shown in FIG. 7C.

Figure 7D:
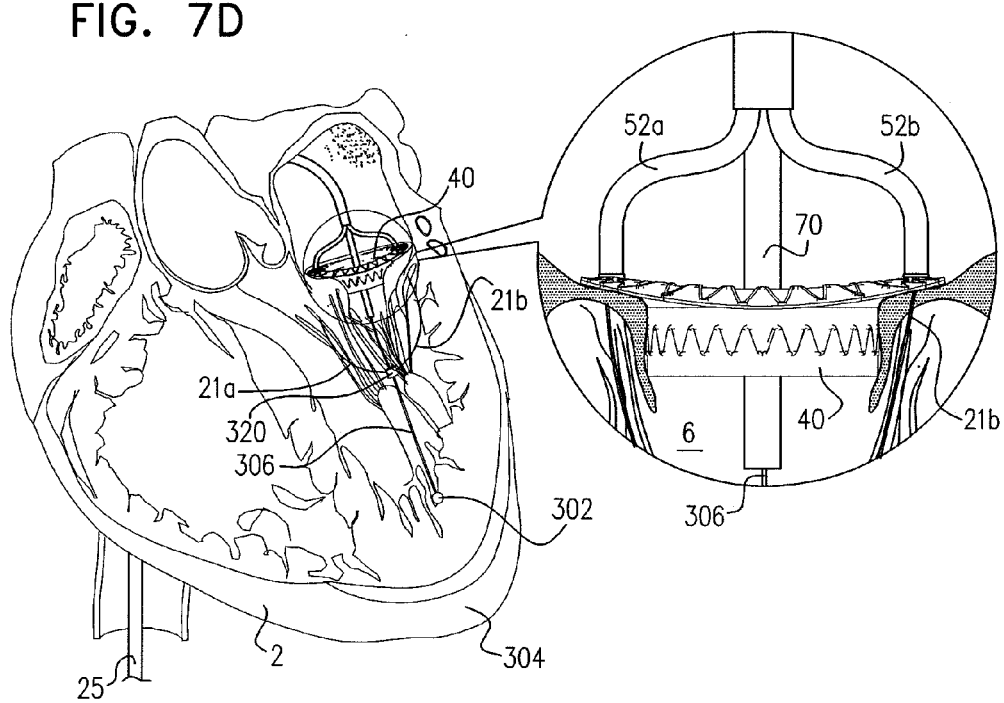
Figure 7E:
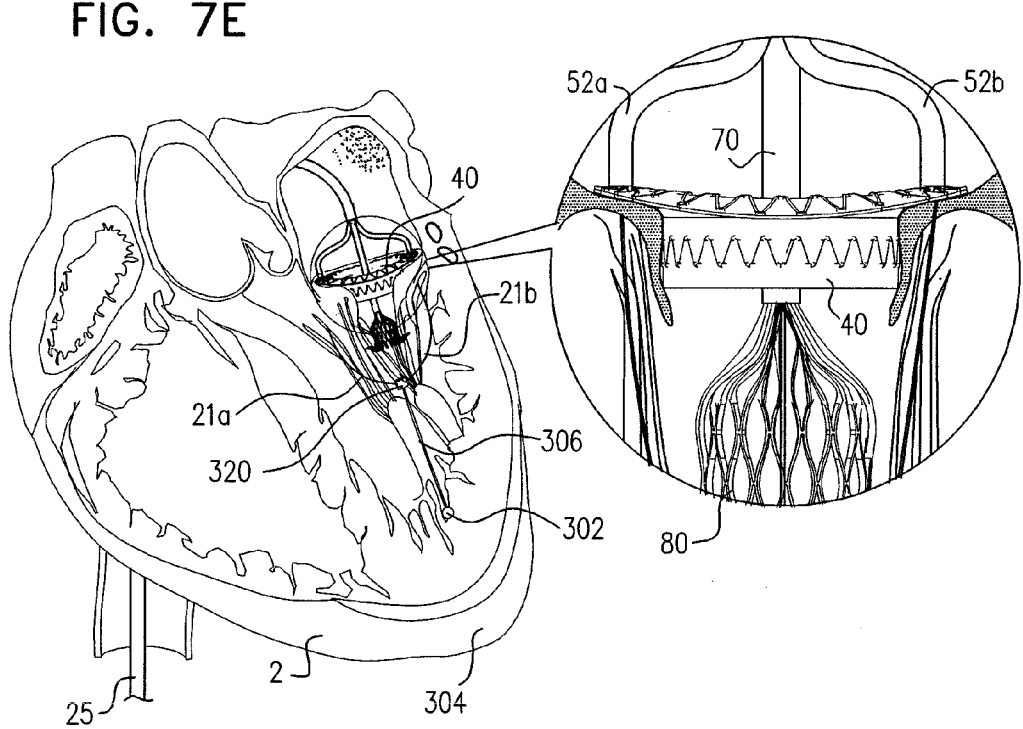

Subsequent to the placement of valve support 40 at the native valve, prosthetic atrioventricular valve 80 is coupled to valve support 40. For some applications, pushing elements 52a and 52b continue to push the valve support against the native valve, during the coupling of the prosthetic valve to the valve support. As described hereinabove, overtube 70 is advanced into ventricle 6, as shown in FIG. 7D. FIG. 7E shows prosthetic valve having been partially deployed in the ventricle. Following the partial deployment of valve 80 in ventricle 6, overtube 70 is pulled proximally to pull valve 80 proximally such that cylindrical element 42 of valve support 40 surrounds a proximal portion of prosthetic valve 80. Valve 80 has a tendency to expand such that valve 80 is held in place with respect to valve support 40 responsively to radial forces acted upon valve support 40 by prosthetic valve 80. During the pulling back of overtube 70, pushing elements 52a and 52b push valve support 40 against the valve, thereby providing a counter force against which overtube 70 is pulled back. For some applications, the pushing of the valve support against the commissures is such that it is not necessary to use anchors for anchoring the valve support to the native valve during the coupling of the prosthetic valve to the valve support. Alternatively, in addition to the pushing elements providing a counter force against which the prosthetic valve is pulled, anchors are used to anchor the valve support to the native valve during the coupling of the prosthetic valve to the valve support.

As described hereinabove, valve 80 comprises a plurality of distal protrusions 84. When valve 80 is pulled proximally, as described hereinabove, protrusions 84 ensnare and engage the native leaflets of the atrioventricular valve. By the ensnaring of the native leaflets, protrusions 84 sandwich the native valve between protrusions 84 and prosthetic valve support 40. Such ensnaring helps further anchor prosthetic valve 80 to the native atrioventricular valve.

Figure 7F:
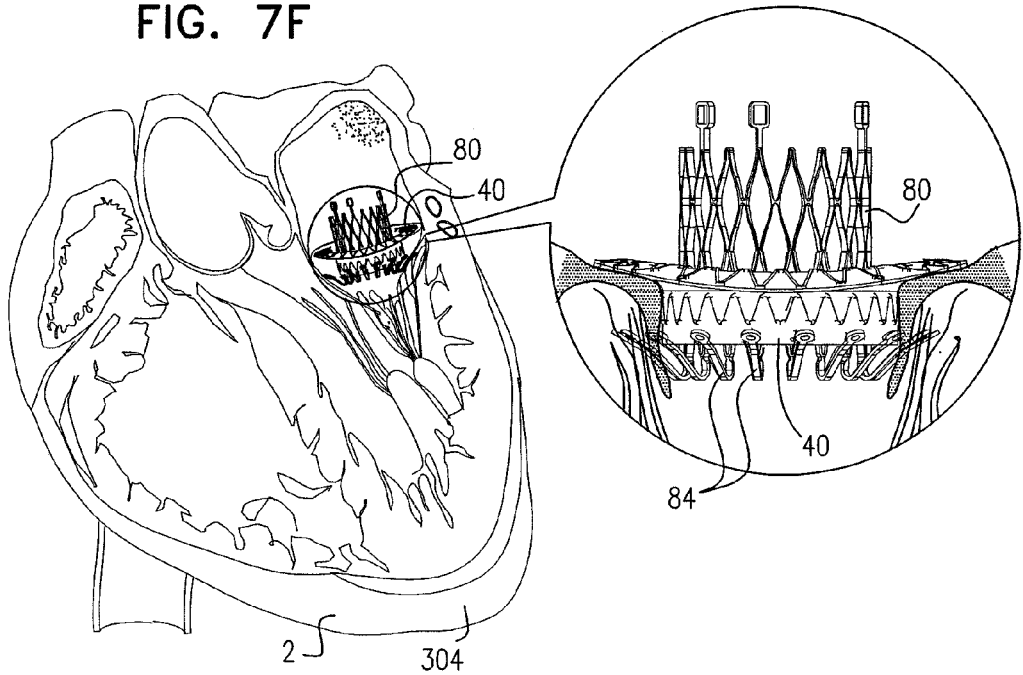

Subsequent to the placement of the prosthetic valve at the native valve, sheath 25, overtube 70, pushing elements 52a and 52b, guide member 21, anchor 302, and guidewire 306 are removed from the patient's body, as shown in FIG. 7F, which shows the prosthetic valve in its deployed state. For some applications, in order to remove guide member 21 from the patient's body, guide member portions 21a and 21b are decoupled from guide member tube 320. For example, the guide member portions may be coupled to the guide member tube via threading, the guide member portions being decoupled from the guide member tube by unscrewing the guide member portions from the guide member tube.

Reference is now made to FIGS. 8A-C which are schematic illustrations of a system 120 comprising an invertible valve support 140, in accordance with some applications of the present invention. Invertible valve support 140 is identical to valve support 40 described herein, with the exception that the cylindrical element of valve support 140 is invertible, as is described hereinbelow. Additionally, the method of advancing toward and implanting valve support 140 at annulus 11 is identical to the methods of advancing toward and implanting valve support 40 at annulus 11, as described hereinabove.

Valve support 140 comprises an annular element 144 (that is identical to annular element 44 described hereinabove) and a cylindrical element 142. Cylindrical element 142 has a first end 150, a second end 152, and a cylindrical body 153 disposed between first and second ends 150 and 152. Cylindrical element 142 is attached to annular element 144 at first end 150 of cylindrical element 142.

During and following implantation of support 140 at annulus 11, as shown in FIG. 8A, cylindrical element 142 is disposed above annular element 144 in a manner in which second end 152 and cylindrical body 153 are disposed above annular element 144 and within atrium 4. One or more elongate guide members 146a and 146b are reversibly coupled to cylindrical element 142 in a vicinity of second end 152. Elongate guide members 146a and 146b facilitate (a) advancement of prosthetic valve 80 therealong and toward valve support 140, and (b) inversion of cylindrical element 142 toward ventricle 6 when at least a portion of valve 80 is deployed within ventricle 6 (as shown in FIG. 8B).

The configuration of valve support 140 as shown in FIG. 8A (i.e., the configuration in which cylindrical element 142 is disposed within atrium 4) eliminates the obstruction of native valve 5 and of leaflets 12 and 14 by any portion of valve support 140. In this manner, valve support 140 may be implanted at valve 5 while valve 5 resumes its native function and leaflets 12 and 14 resume their natural function (as shown by the phantom drawing of leaflets 12 and 14 in FIG. 8A which indicates their movement). This atrially-inverted configuration of valve support 140 reduces and even eliminates the amount of time the patient is under cardiopulmonary bypass. Only once prosthetic valve 80 is delivered and coupled to valve support 140 and cylindrical element 142 is thereby ventricularly-inverted, native leaflets 12 and 14 are pushed aside (FIG. 8B).

FIG. 8B shows the inversion of cylindrical element 142 by the partial positioning and deployment of prosthetic valve 80 within ventricle 6. Elongate guide members 146a and 146b are reversibly coupled to prosthetic valve 80 and extend within overtube 70. Following the full deployment of valve 80 and the coupling of valve 80 to valve support 140, elongate guide members 146a and 146b are decoupled from prosthetic valve 80 and from cylindrical element 142. For example, a cutting tool may be used to decouple elongate members 146a and 146b from the valve support 140. Alternatively, elongate members 146a and 146b may be looped through the cylindrical element 142, such that both ends of each elongate member 146a and 146b remain outside of the patient's body. The operating physician decouples elongate members 146a and 146b from valve support 140 by releasing one end of each of elongate members 146a and 146b and pulling on the other end, until elongate members 146a and 146b are drawn from valve support 140 and removed from within the body of the patient.

FIG. 8C shows prosthetic valve 80 coupled to valve support 140. Valve 80 is identical to the valve described hereinabove.

Reference is now made to FIGS. 9A-E, which are schematic illustrations of the advancement of an invertible prosthetic valve support 300 toward a native atrioventricular valve of a patient, and inversion of the valve support, in accordance with some applications of the present invention. Prosthetic valve support 300 is used to anchor prosthetic valve 80 to native valve 5 in a generally similar manner to that described with reference to prosthetic valve support 40.

Figure 9A:
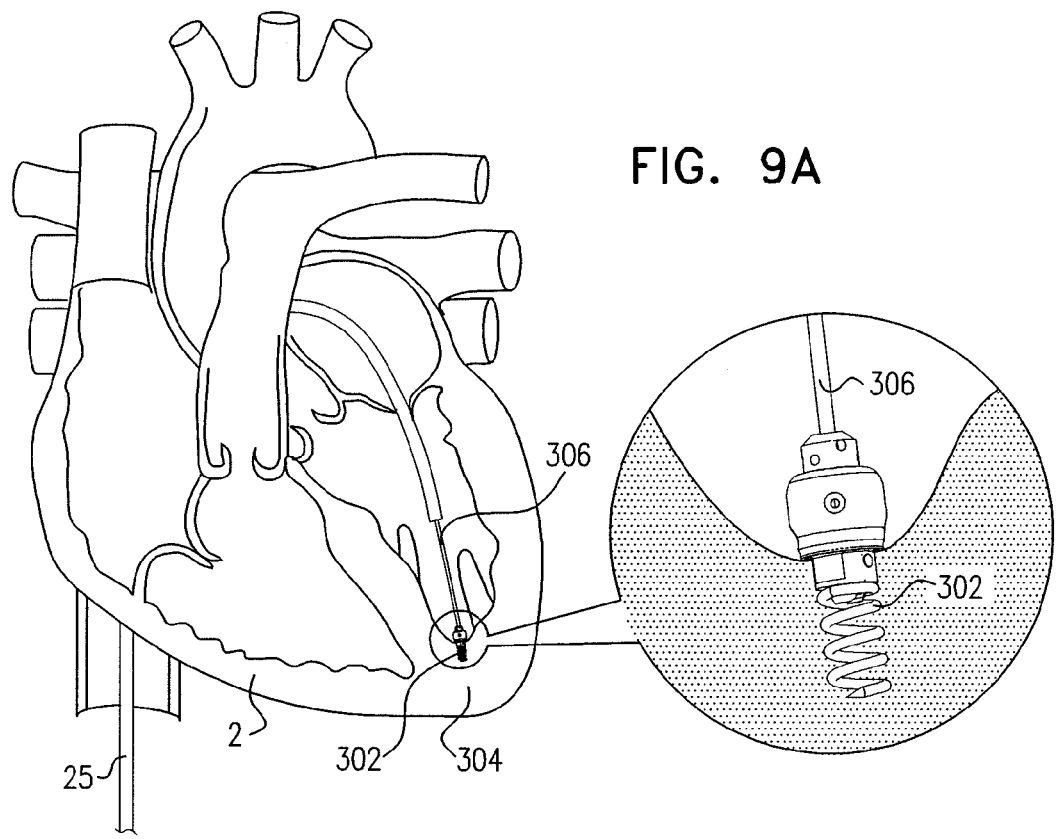
FIGS. 9A-D are schematic illustrations of the advancement of an invertible prosthetic valve support toward a native atrioventricular valve of a patient, in accordance with some applications of the present invention.
Figure 9B:
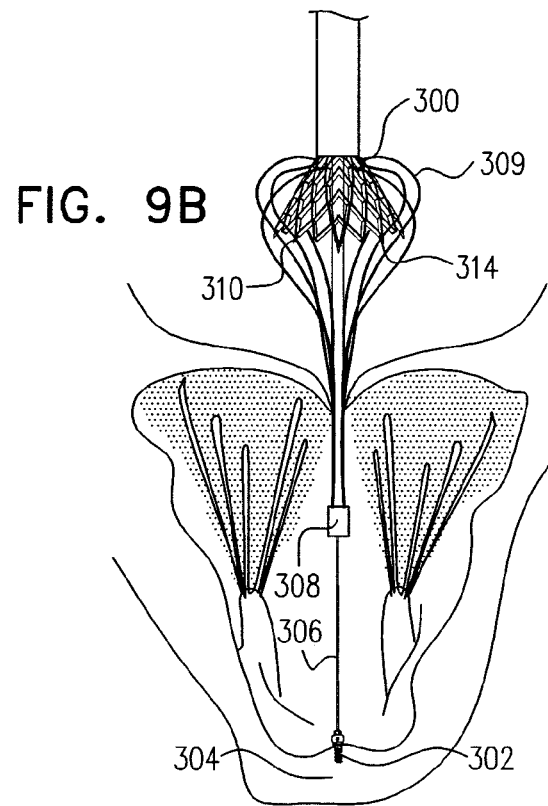
Figure 9C:
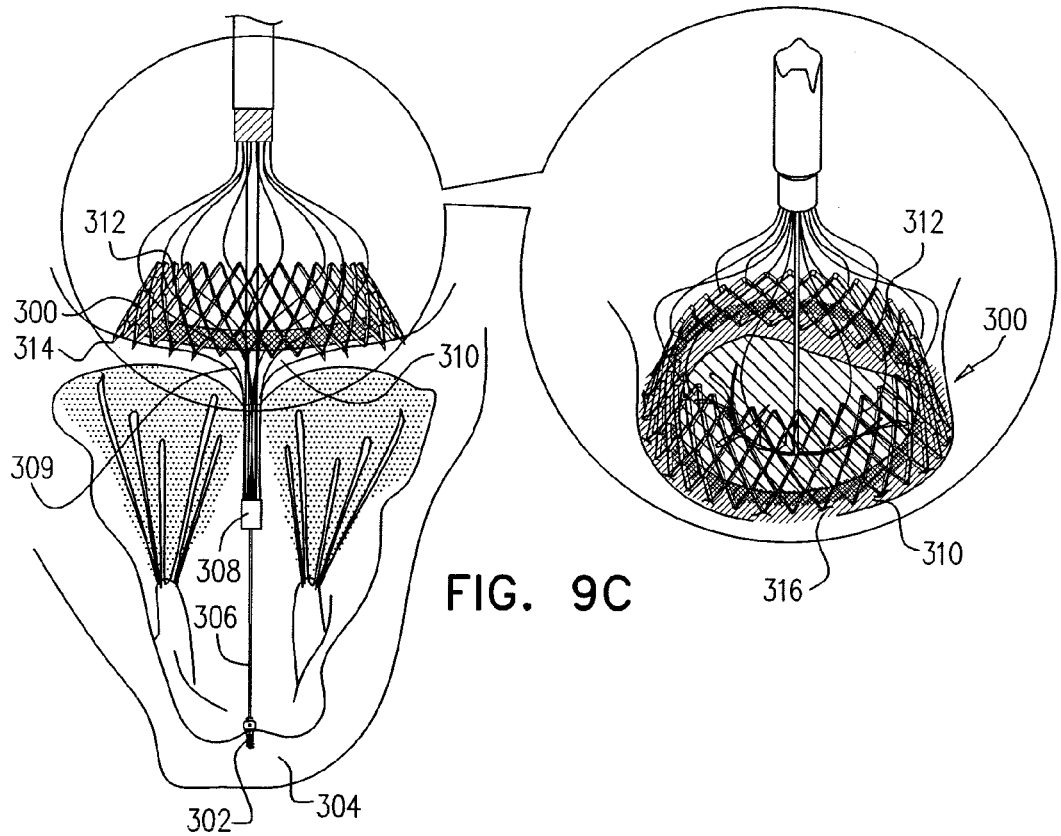
Figure 9D:
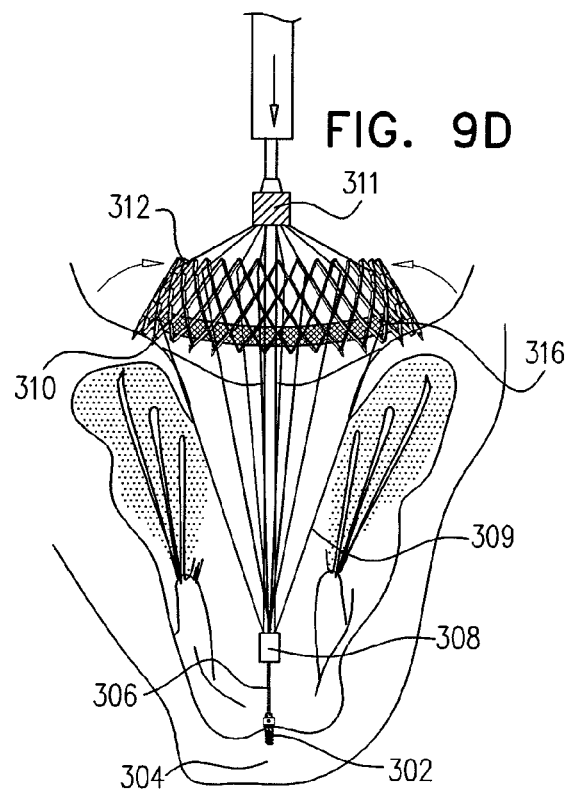
Figure 9E:
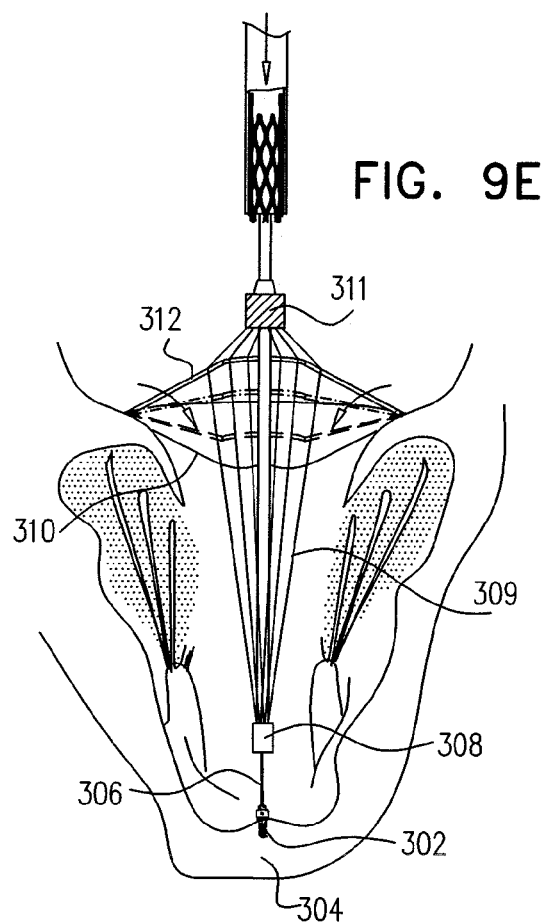
FIG. 9E is a schematic illustration of inversion of the invertible prosthetic valve support at the native valve, in accordance with some applications of the present invention.

During a typical procedure, anchor 302 is advanced toward the vicinity of apex 304 of heart 2, via sheath 25, and is anchored to the vicinity of the apex, as shown in FIG. 8A. A guidewire 306 extends proximally from anchor. A distal tensioning element 308 (e.g., a plunger) is advanced over guidewire 306 into ventricle 6, and prosthetic valve support 300 is advanced out of the distal end of sheath 25, as shown in FIG. 9B. A first end 310 of prosthetic valve support 300 (which at this stage is the distal end of the prosthetic valve support), comprises barbs 314 (shown in FIG. 9B), or other anchoring elements for anchoring the first end of the prosthetic valve support to tissue of native valve 5. Prosthetic valve support 300 is pushed distally such that the barbs are pushed into the native valve tissue, thereby anchoring the first end of the prosthetic valve support to the native valve, as shown in FIG. 9C. A plurality of wires 309 pass from distal tensioning element 308 to a proximal tensioning element 311 (shown in FIG. 9D), via a second end 312 of valve support 300 (which at this stage is the proximal end of the prosthetic valve support). For some applications, a sealing element 316 is disposed circumferentially around a surface of the invertible prosthetic valve support that is initially an inner surface of the invertible prosthetic valve support (a shown in FIGS. 8A-D). For example, the sealing material may be latex, dacron, or another suitable biocompatible sealing material.

Figure 9F:
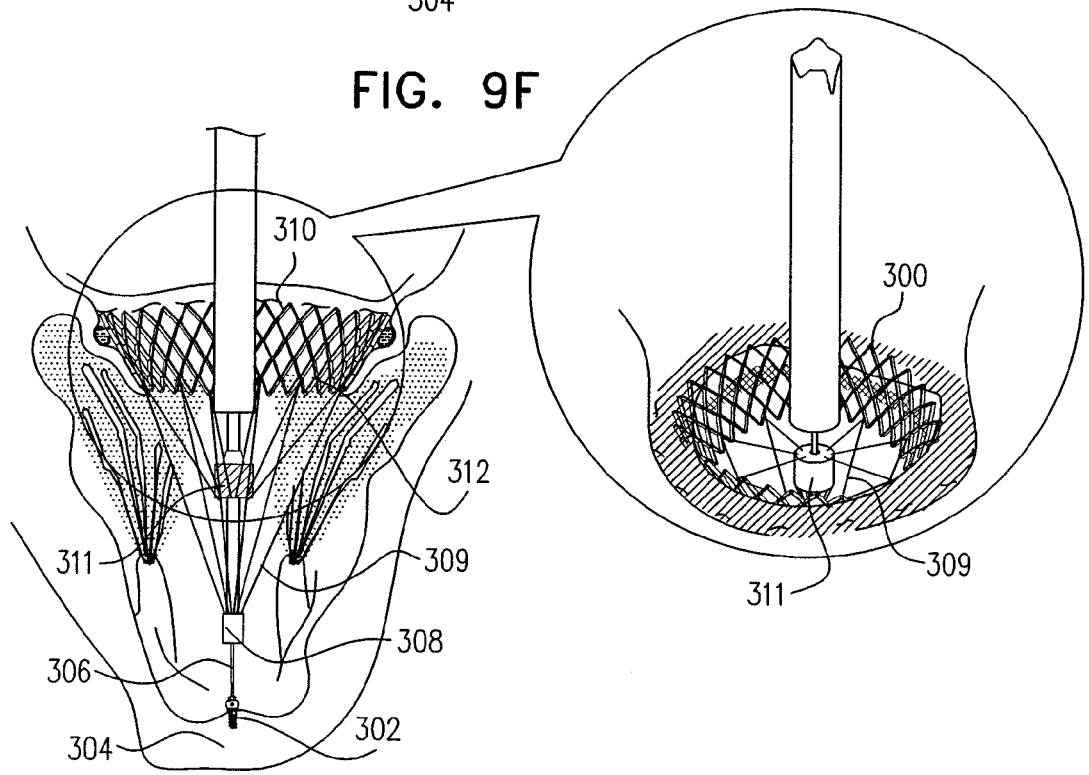
FIGS. 9F-H are schematic illustrations of the advancement of a prosthetic valve and the coupling of the prosthetic valve to the invertible valve support, in accordance with some applications of the present invention.

Subsequent to the anchoring of first end 310 of prosthetic valve support 300 to native valve tissue (as shown in FIG. 9C), distal tensioning element 308 is further advanced distally into ventricle 6, and proximal tensioning element 311 is advanced toward the ventricle. As shown in the transition from FIG. 9D-F, as the proximal tensioning element passes through the valve support, wires 309 cause valve support 300 to invert, by pulling second end 312 of the valve support through first end 310 of the valve support. Subsequent to the inversion of the valve support, sealing material 316 is disposed circumferentially around the outside of the valve support, thereby providing a seal at the interface between valve support 300 and native valve 5.

Figure 9G:
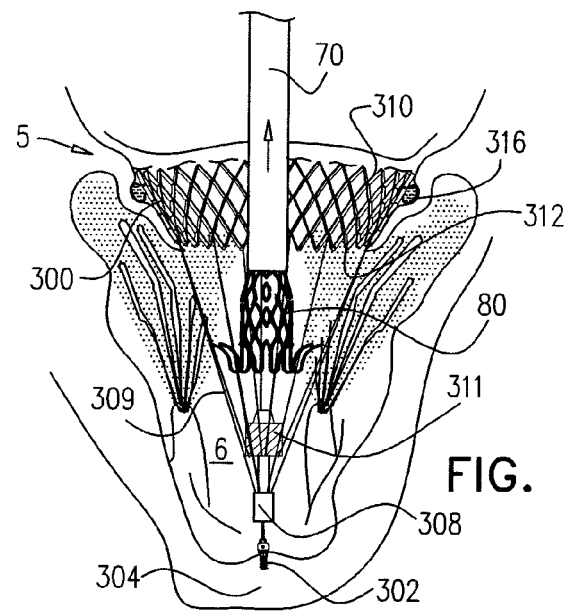
Figure 9H:
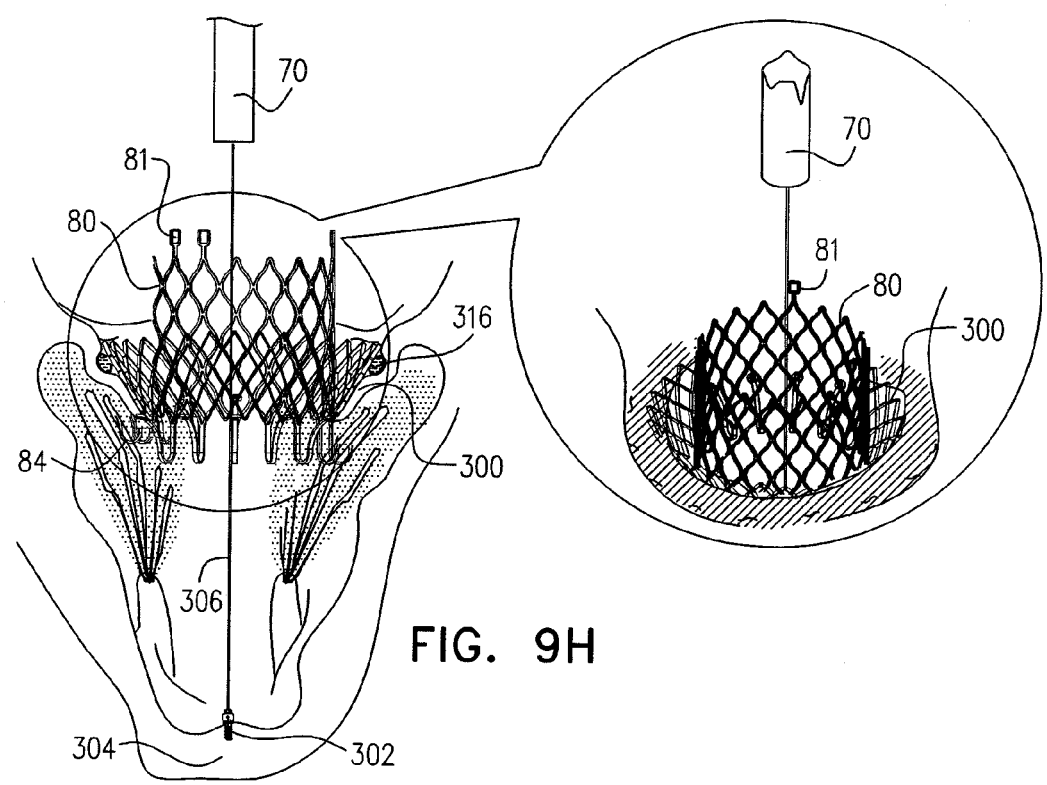

Reference is now made to FIGS. 9G-H, which are schematic illustrations of the deployment of prosthetic valve 80 and the coupling of the prosthetic valve to invertible valve support 300, in accordance with some applications of the present invention.

The deployment of prosthetic valve 80 is generally similar to the techniques described hereinabove with reference to FIGS. 2H-J. The valve is partially deployed in ventricle 6, via overtube 70. Following the partial deployment of valve 80 in ventricle 6, overtube 70 is pulled proximally (as shown in FIG. 8G) to pull valve 80 proximally such that valve support 300 surrounds a proximal portion of prosthetic valve 80, as shown in FIG. 8H. Valve 80 has a tendency to expand such that valve 80 is held in place with respect to valve support 300 responsively to radial forces acted upon valve support 300 by prosthetic valve 80.

As described hereinabove, for some applications, valve 80 comprises a plurality of distal protrusions 84. When valve 80 is pulled proximally, protrusions 84 ensnare and engage the native leaflets of the atrioventricular valve. By the ensnaring of the native leaflets, protrusions 84 sandwich the native valve between protrusions 84 and prosthetic valve support 300. Such ensnaring helps further anchor prosthetic valve 80 to the native atrioventricular valve.

Additionally, as shown in FIG. 9H, and as described hereinabove, valve 80 comprises one or more (e.g., a plurality, as shown) coupling elements 81 at the proximal end of valve 80. Overtube 70, which facilitates the advancement of prosthetic valve 80, is reversibly coupled to valve 80, via coupling elements 81.

Subsequent to the coupling of valve 80 to valve support 300, overtube 70, distal and proximal tensioning elements 308 and 311, and wires 309 are removed from the patient's body, via sheath 25. Typically, wires 309 are cut, in order to facilitate the removal of the wires from the patient's body. Guidewire 306 and anchor 302 are removed from the patient's body by detaching the anchor from apex 304, and withdrawing the anchor and the guidewire, via sheath 25.

Figure 10:
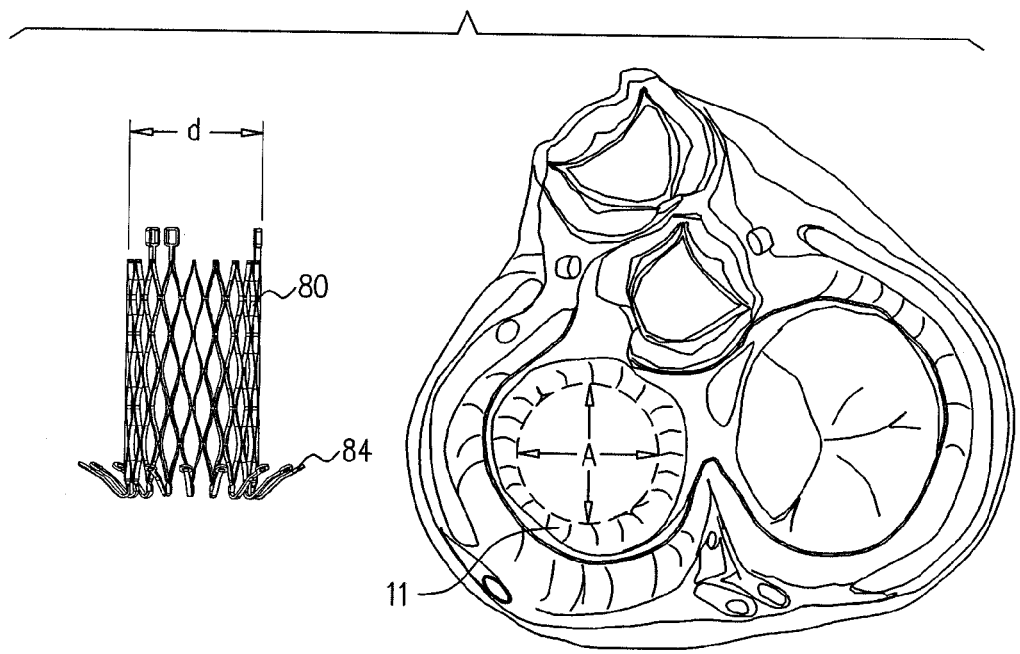
FIG. 10 is a schematic illustration of a prosthetic valve, the cross-sectional area of which is smaller than the area defined by the patient's native valve annulus, in accordance with some applications of the present invention.

Reference is now made to FIG. 10, which is a schematic illustration of prosthetic valve 80, for placing inside atrioventricular valve 5 of the patient, in accordance with some applications of the present invention. The frame of the prosthetic valve has a diameter d, and a corresponding cross-sectional area. Native annulus 11, which is typically saddle-shaped, defines an area A, as shown. For some applications, area A, which is defined by the native annulus is measured, e.g., using a measuring ring. A prosthetic valve is chosen to be placed in the annulus, the cross-sectional area of the prosthetic valve being less than 90% (e.g., less than 80%, or less than 60%) of area A. For some applications, placing a prosthetic valve inside the native valve with the dimensions of the native valve annulus and the prosthetic valve as described, facilitates sealing of the prosthetic valve with respect to the native valve, by the native valve leaflets closing around the outer surface of the prosthetic valve.

For some applications, in order to facilitate the sealing of the native valve around the outer surface of the prosthetic valve, a material is placed on the outer surface of the prosthetic valve in order to provide a sealing interface between the prosthetic valve and the native valve. For example, a smooth material that prevents tissue growth (e.g., polytetrafluoroethylene (PTFE), and/or pericardium) may be placed on the outer surface of the prosthetic valve. Alternatively or additionally, a material that facilitates tissue growth (such as dacron) may be placed on the outer surface of the prosthetic valve, in order to (a) act as a sealing interface between the native valve and the prosthetic valve, and (b) facilitate tissue growth around the prosthetic valve to facilitate anchoring and/or sealing of the prosthetic valve.

Reference is now made to FIGS. 11A-D, which are schematic illustrations of prosthetic valve 80, in accordance with some applications of the present invention. For some applications, protrusions 84 are disposed on the valve on portions 400 of the valve that are placed adjacent to the anterior and posterior leaflets of the native valve, and the valve does not includes protrusions on portions 402 of the valve that are placed adjacent to the commissures of the native valve.

Figure 11A:
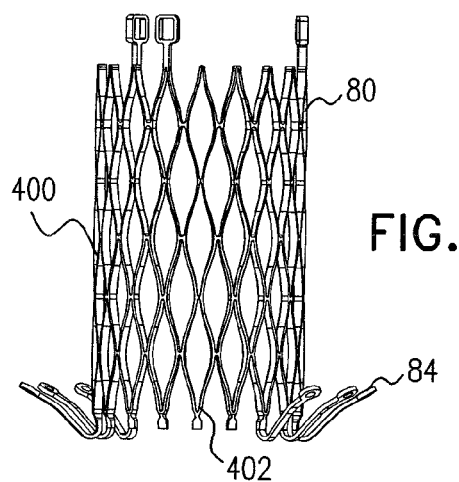
FIGS. 11A-D are schematic illustrations of a prosthetic valve that defines protrusions from portions of the distal end of the valve, in accordance with some applications of the present invention.
Figure 11B:
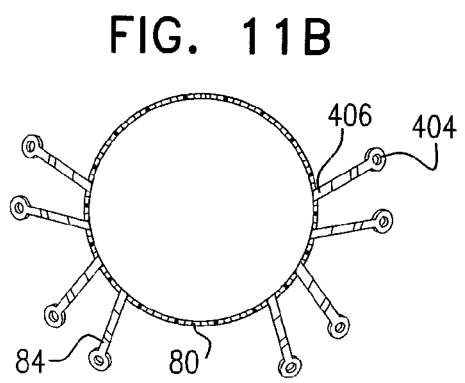
Figure 11C:
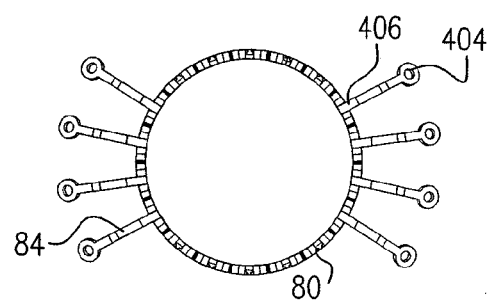
Figure 11D:
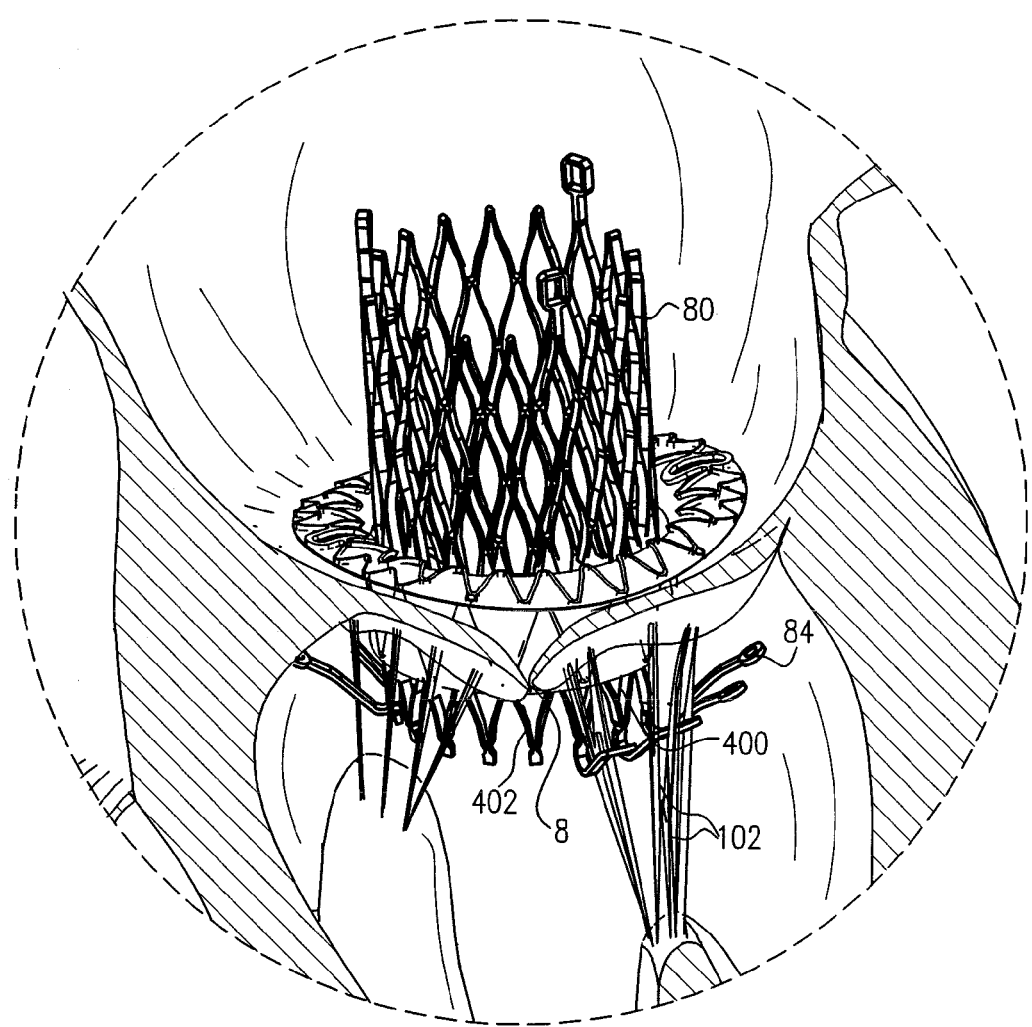

FIGS. 11B-D show bottom views (i.e., views of the distal ends) of respective configurations of prosthetic valve 80 and protrusions 84. The protrusions converge from the proximal ends 404 of the protrusion to the distal ends 406 of the protrusions. The protrusions are configured such as to ensnare chordae tendineae, and to pull the chordae tendineae toward each other when the prosthetic valve is pulled proximally, due to the convergence of the snares with respect to each other. FIG. 11D shows the prosthetic valve deployed at native valve 5. As shown, the protrusions ensnare chordae tendineae 102 of the patient. The protrusions facilitate sealing and anchoring of the prosthetic valve with respect to the native valve by pulling the chordae tendineae toward each other, as described. As described hereinabove, for some applications the prosthetic valve does not define protrusions 84 on portions 402 that are placed next to the native commissures, e.g., commissure 8, shown in FIG. 11D.

For some applications, a first set of protrusions 84 from the distal end of prosthetic valve 80 are disposed the within a first circumferential arc with respect to a longitudinal axis of the prosthetic valve, on a first side of the distal end of the prosthetic valve, the first side of the distal end being configured to be placed adjacent to the anterior leaflet of the native valve. A second set of protrusions are disposed the within a second circumferential arc with respect to a longitudinal axis of the prosthetic valve, on a second side of the distal end of the prosthetic valve, the second side of the distal end being configured to be placed adjacent to the posterior leaflet of the native valve.

The first and second sets of protrusions are disposed so as to provide first and second gaps therebetween at the distal end of the prosthetic valve. Typically, at least one of the gaps between the two sets of protrusions has a circumferential arc of at least 20 degrees (e.g., at least 60 degrees, or at least 100 degrees), and/or less than 180 degrees (e.g., less than 140 degrees), e.g., 60-180 degrees, or 100-140 degrees. Further typically, one or both of the first and second circumferential arcs defines an angle of at least 25 degrees (e.g., at least 45 degrees), and/or less than 90 degrees (e.g., less than 75 degrees), e.g., 25-90 degrees, or 45-75 degrees.

Valve guide members (e.g., guide members 21a and 21b, and/or delivery lumen 27a and 27b, as described hereinabove) are delivered to commissures of the native valve, and guide the valve such that the first and second circumferential arc are aligned with respective leaflets of the native valve and such that the first and second gaps are aligned with respective commissures of the native valve.

Reference is now made to FIGS. 12A-C, which are schematic illustrations of prosthetic valve 80, the valve defining distal protrusions 84 that are disposed sinusoidally around the circumference of the valve, in accordance with some applications of the present invention. For some applications the protrusions are shaped sinusoidally, in order to conform with the saddle-shape of native valve annulus 11, thereby facilitating the sandwiching of the native valve leaflets between the protrusions and valve support 40. As shown, the peaks of the sinusoid that is defined by the protrusions is disposed on portions 402 that are placed next to the native commissures and the troughs of the sinusoid is placed on portions of the valve that are placed in the vicinity of the centers of the anterior and posterior leaflets of the native valve. As shown in FIG. 12C, for some applications the distal end of the prosthetic valve defines a sinusoidal shape.

Reference is now made to FIGS. 1A-D, 2A-K, 3A-D, 4A-C, 5A-D, 6A-B, 7A-F, 8A-C, 9A-H, 10, 11A-D, and 12A-C. It is to be noted that valve support 40 may be invertible as described hereinabove with respect to valve supports 140 and 300, with reference to FIGS. 8A-C, and 9A-H. It is to be further noted that valve supports 140 and 300 may be used in conjunction with one or more of the elements for facilitating sealing of the native valve with respect to a valve support or a valve that is described with reference to FIGS. 3A-D, 4A-C, 5A-D, and 6A-B. For example, valve supports 140 and 300 may be used with sealing balloon 90, commissural anchors 100a and 100b, grasping elements 106a and 106b, and/or sealing material 110. It is still further noted that valve supports 140 and 300 may be implanted using a guide member that defines a looped portion between commissures 8 and 10, as described with reference to FIGS. 7A-F. It is further noted that any of the applications described herein can be used in conjunction with valves having configurations as described with reference to FIGS. 10-12C.

The systems described herein are advanced toward valve in a transcatheter procedure, as shown. It is to be noted, however, that the systems described herein may be advanced using any suitable procedure, e.g., minimally-invasive or open-heart. It is to be further noted that valve supports and prosthetic valves herein may be used to replace native mitral valves or native tricuspid valves.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. A method, comprising:
   placing an annular element of a prosthetic valve support against an annulus of a native atrioventricular valve of a patient;
   subsequently, delivering a prosthetic valve, having a main frame and one or more snares coupled to the main frame, to the native atrioventricular valve; and
   deploying the prosthetic valve at the native valve, the step of deploying comprising:
      ensnaring at least one leaflet of the native valve with the one or more snares, and
      expanding the prosthetic valve such that an outer surface of the main frame of the prosthetic valve defines a cross-sectional area that is not more than 90% of an area defined by an annulus of the native atrioventricular valve.

2. The method according to claim 1, further comprising:
   determining the area defined by the annulus of the native atrioventricular valve of the patient; and
   selecting the prosthetic valve by determining that the outer surface of the main frame of the prosthetic valve defines the cross-sectional area that is not more than 90% of the area defined by the annulus,
   the selecting of the prosthetic valve facilitating sealing of the native valve with respect to the prosthetic valve by facilitating closing of leaflets of the native valve around the prosthetic valve, upon deployment of the prosthetic valve.

3. The method according to claim 2, wherein selecting the prosthetic valve comprises selecting a prosthetic valve having a material disposed on an outer surface thereof.

4. The method according to claim 3, wherein selecting the prosthetic valve comprises selecting a prosthetic valve having a material that prevents tissue growth disposed on an outer surface thereof.

5. The method according to claim 3, wherein selecting the prosthetic valve comprises selecting a prosthetic valve having a material that promotes tissue growth disposed on an outer surface thereof.

6. The method according to claim 1, wherein expanding the prosthetic valve comprises expanding the prosthetic valve such that the outer surface of the main frame of the prosthetic valve defines a cross-sectional area that is less than 80% of the area defined by the annulus.

7. The method according to claim 6, wherein expanding the prosthetic valve comprises expanding the prosthetic valve such that the outer surface of the main frame of the prosthetic valve defines a cross-sectional area that is less than 60% of the area defined by the annulus.

8. The method according to claim 2, wherein deploying the prosthetic valve comprises deploying at least a portion of the prosthetic valve within the prosthetic valve support.

9. The method according to claim 8, wherein deploying the at least the portion of the prosthetic valve within the prosthetic valve support comprises expanding the at least the portion of the prosthetic valve such that the at least the portion of the prosthetic valve applies a radial force to the prosthetic valve support.

10. The method according to claim 1, wherein the one or more snares are coupled to a downstream portion of the main frame, and wherein delivering the prosthetic valve comprises delivering the prosthetic valve having the one or more snares coupled to the downstream portion of the main frame.

11. The method according to claim 1, wherein deploying the prosthetic valve comprises expanding at least a portion of the prosthetic valve within the prosthetic valve support.

12. The method according to claim 1, wherein placing the annular element against the annulus comprises pushing the annular element against the annulus using a percutaneously-advanceable pushing element, and wherein the method further comprises:
   after placing the annular element against the annulus, and during the deployment of the prosthetic valve, holding the annular element against the annulus by continuing to push the annular element against the annulus using the pushing element; and
   subsequently, removing the pushing element from the annular element.

* * * * *